(12) United States Patent
Bender

(10) Patent No.: US 9,522,863 B2
(45) Date of Patent: Dec. 20, 2016

(54) XYLENE SEPARATION PROCESS

(71) Applicant: ExxonMobil Chemical Patents Inc., Baytown, TX (US)

(72) Inventor: Timothy P. Bender, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 247 days.

(21) Appl. No.: 14/580,452

(22) Filed: Dec. 23, 2014

(65) Prior Publication Data
US 2015/0246860 A1    Sep. 3, 2015

Related U.S. Application Data

(60) Provisional application No. 61/946,052, filed on Feb. 28, 2014.

(51) Int. Cl.
*C07C 7/13*  (2006.01)
*C07C 6/12*  (2006.01)

(52) U.S. Cl.
CPC  *C07C 7/13* (2013.01); *C07C 6/123* (2013.01)

(58) Field of Classification Search
CPC .............. C07C 7/13; C07C 7/00; C07C 7/12; C07C 7/005; C07C 15/00; C07C 15/02; C07C 15/08; C07C 15/24; C07C 15/067; C07C 15/073; C07C 6/06; B01D 15/10
USPC .............. 585/826, 800, 828, 820, 821, 822, 823,585/825, 829; 210/198.2, 656, 659
See application file for complete search history.

(56) References Cited

U.S. PATENT DOCUMENTS

| | | |
|---|---|---|
| 3,040,777 A | 6/1962 | Carson et al. |
| 3,201,491 A | 8/1965 | Stine et al. |
| 3,422,848 A | 1/1969 | Liebman et al. |
| 3,706,812 A | 12/1972 | Rosset et al. |
| 3,761,533 A | 9/1973 | Otani et al. |
| 4,006,197 A | 2/1977 | Bieser |
| 4,029,717 A | 6/1977 | Healy et al. |
| 4,031,156 A | 6/1977 | Geissler et al. |
| 4,992,618 A | 2/1991 | Kulprathipanja |
| 5,750,820 A | 5/1998 | Wei |
| 5,884,777 A | 3/1999 | Pan et al. |
| 6,017,448 A | 1/2000 | Hotier et al. |
| 6,110,364 A | 8/2000 | Hotier et al. |
| 6,149,874 A | 11/2000 | Hotier |
| 7,396,973 B1 | 7/2008 | Winter |
| 7,582,207 B2 | 9/2009 | Hotier et al. |
| 8,008,536 B2 | 8/2011 | Winter et al. |
| 8,168,845 B2 | 5/2012 | Porter et al. |
| 8,481,798 B2 | 7/2013 | Schaefer et al. |
| 8,529,757 B2 | 9/2013 | Go et al. |
| 8,569,564 B2 | 10/2013 | Porter et al. |
| 8,580,120 B2 | 11/2013 | Porter |
| 8,802,913 B2 | 8/2014 | Porter |
| 2006/0199989 A1 | 9/2006 | Frey |
| 2009/0036726 A1 | 2/2009 | Leflaive et al. |

FOREIGN PATENT DOCUMENTS

EP    0 722 356    7/1996

*Primary Examiner* — Sharon Pregler

(57) ABSTRACT

A process is described for separating paraxylene from a multicomponent fluid mixture of C8 aromatics, and more particularly to a process for separating paraxylene from such a fluid mixture by means of adsorption apparatus, such as moving-bed or simulated moving-bed adsorption apparatus. A process is also described for making paraxylene by making a mixture of C8 aromatics and separating paraxylene from the mixture by means of a simulated moving-bed adsorption apparatus.

24 Claims, 1 Drawing Sheet

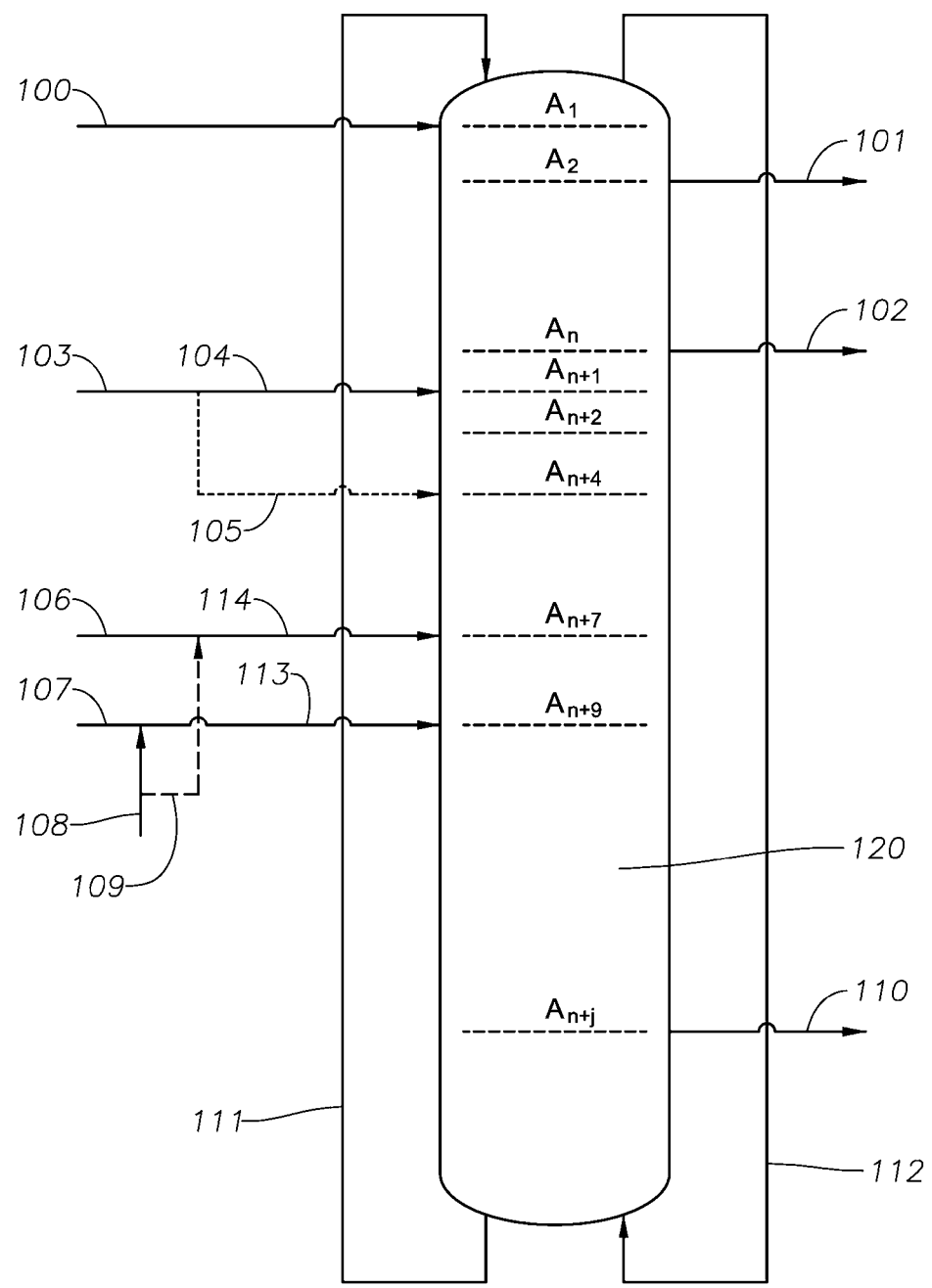

XYLENE SEPARATION PROCESS

CROSS REFERENCE TO RELATED APPLICATIONS

This application claims priority to and the benefit of U.S. Provisional Application No. 61/946,052, filed Feb. 28, 2014, the disclosure of which is incorporated herein by reference in its entirety.

FIELD OF THE INVENTION

The invention relates to a process for separating paraxylene from a multicomponent fluid mixture of C8 aromatics, and more particularly to a process for separating paraxylene from such a fluid mixture by means of an adsorption apparatus, such as a moving-bed or simulated moving-bed adsorption apparatus. The invention further relates to a process for making paraxylene by making a mixture of C8 aromatics and separating paraxylene from the mixture by means of a simulated moving-bed adsorption apparatus.

BACKGROUND OF THE INVENTION

Various means are currently available to separate the components of a multicomponent fluid mixture. If the densities of the components differ sufficiently, the effects of gravity over time may be adequate to separate the components. Depending on the quantities of the components involved, a centrifuge may be used to more rapidly separate components with different densities. Alternatively, distillation may be used to separate components with different boiling points.

Some fluid mixtures comprise components which have similar boiling points, and in such cases, separation by distillation may be a difficult and an inefficient means to separate these components. Too many contaminants, e.g., unwanted components, also may evaporate along with (or fail to evaporate from) the desired component(s), or the separation may require high energy expenditures due to the recycling through the distillation process that may be necessary to attain a desired degree of separation or purity.

In view of these and other deficiencies of these aforementioned processes, adsorption often has been preferred as a process for separating the components from a multicomponent fluid mixture to obtain relatively pure products.

The efficiency of an adsorption process may be partially dependent upon the amount of the surface area of the adsorbent solids which is available for contact with a fluid mixture. The surface area available may be more than just the superficial, external surface of the solids. Suitable solids also may have internal spaces. Such internal spaces may comprise pores, channels, or holes in the surface of the solids and may run throughout the solids, much as in sponges. Thus, the fluid contacts not only the superficial surface, but penetrates into the solids. Internal spaces increase the contact surface between the fluid and the solids in an adsorption process by concentrating them in a confined space. Examples of solids with internal void spaces include solids described as molecular sieves. The volumetric amount of components that may be adsorbed by a molecular sieve is termed the molecular sieve capacity.

In an adsorption process, separation of the fluid components may be accomplished because the adsorbent solid material may have a physical attraction for one or more of the components of the mixture in preference to other components of the mixture. Although all of the components of a mixture may be attracted in varying degrees to the material, there is a preference engineered into the process, such that predominantly the desired component(s) may be attracted and remain with the material in preference over all others. Therefore, even if less preferred components of a mixture initially come into contact with a portion of the material, because of the stronger attraction of the material for the desired component(s) of the mixture, the less preferred component(s) may be displaced from the material by the desired, and more strongly preferred, component(s). Although the fluid mixture entering an adsorbent bed might be composed of multiple components, the fluid mixture passed through the adsorbent bed would be depleted in the component(s) which are more preferentially adsorbed into the adsorbent. The concentration of the less preferentially adsorbed component(s), based upon the total concentration of more and less preferentially components, would be greater in the effluent from the bed than in the feed to the bed.

In adsorption processes using adsorbent solids, separation occurs for a period of time, but eventually all the available surface sites on and in the solids are taken up by the desired component(s) or are blocked by concentrations of unwanted components. At that point, little significant additional adsorption of component(s) from the mixture is likely to occur, and the fluid mixture which might be withdrawn from the chamber may be insignificantly changed by further exposure to the solids. The adsorption step of the process is thus ended, and the component(s) which have been adsorbed by the solids can then be removed from the solids, so as to effect separation and permit reuse of the solids.

A suitable adsorption apparatus or system might first permit adsorption of a product comprising the desired component(s) by the solids and later treat the solids to cause them to release the product and permit recovery of this product. Such an adsorption apparatus or system might comprise a "moving-bed" which permits movement of a tray or bed of the solids through a chamber, such that at different locations, the solid is subjected to different steps of an adsorption process, e.g., adsorption, purification, and desorption. These steps will be understood more clearly by the description below. Nevertheless, moving the solids through an adsorption apparatus may be difficult and involve complex machinery to move trays or beds. It also may result in loss of the solids by attrition. To avoid these problems, some adsorption apparatus and systems have been designed to "simulate" moving the tray(s) or bed(s) to the locations, e.g., zones, of different steps of an adsorption process. Simulation of the movement of the tray(s) or bed(s) may be accomplished by (1) maintaining a continuous, circulating flow of bulk fluid through the tray(s) or bed(s), while (2) varying, over time, the location of feed streams to the circulating bulk fluid, as well as the location of withdrawal streams from the circulating bulk fluid. The location of feed and withdrawal streams may be varied by use of a system of conduits which permits directing and redirecting the streams of fluids into the chamber to create different zones at different times. As these stream changes occur, the solids are eventually employed in different steps in an adsorption process as though the solids were moving in a countercurrent manner to the flow of the circulating bulk fluid through the chamber.

The different zones within an adsorption apparatus or system may be described by a particular step of the adsorption process performed within each zone, for example, (1) an adsorption step in an adsorption zone, (2) a purification step in a purification zone, and (3) a desorption step in the desorption zone. The bulk fluid, which circulates through the adsorption apparatus or system flows in a continuous sequence through the desorption zone, and then through the purification zone, and then through the adsorption zone. The simulated movement of the adsorbent beds occurs in the countercurrent direction of the flow of circulating bulk fluid. Thus, adsorbent beds, in a simulated manner, move in a continuous sequence, first through the adsorption zone, and then through the purification zone, and then through the desorption zone.

The circuit of bulk fluid flow is completed by passing circulating fluid from the purification zone to the adsorption zone and then to the desorption zone, et. seq. One or more buffer zones may be inserted between these zones, for example, between the adsorption zone and the desorption zone. A more detailed explanation of the zones of the adsorption process follows.

Adsorption Zone: A feed stream comprising C8 aromatics, e.g., orthoxylene (OX), metaxylene (MX), paraxylene (PX), and ethylbenzene (EB), is fed into the adsorption apparatus or system. The portion of the apparatus or system into which the feed stream is being fed and carried along with circulating fluid is termed an "adsorption zone." The adsorption zone may comprise a plurality of beds of adsorbent material in a vessel. In the adsorption zone, the fluid comes into contact with the adsorbent material, and the desired component (PX) is adsorbed by the adsorbent material. As noted above, other components (MX, OX and EB) may also be adsorbed, but preferably to a lesser extent. This preferential adsorption may be achieved by the selection of an adsorbent material, e.g., an adsorbent solid, which has a preference for adsorbing the desired component (PX) from the multicomponent feedstream. Although only the desired component (PX) may have been adsorbed by the solids, other less preferentially adsorbed components (MX, OX and EB) of the fluid mixture may still remain in void spaces between the solids and possibly, in the pores, channels, or holes within the solids. The flow of the circulating bulk fluid through the adsorbent beds will tend to carry the unwanted components (MX, OX and EB) through the adsorbent material. These unwanted components (MX, OX and EB) preferably are removed from the solids before the desired component (PX) is recovered from the solids, so that they are not recovered along with the product.

Purification Zone: After adsorption, the next step is to purify or rectify the adsorbent beds, comprising adsorbed desired component (PX), in the adsorption chamber. In the literature, the purification zone is sometimes referred to as the rectification zone. In this step, beds of adsorbent material may be moved or the location of feed and effluent streams may be changed. For example, the feed point of the multicomponent feed stream may be moved from a first bed to a second bed located downstream from the first bed, in terms of the direction of flow of the circulating bulk fluid through the beds. Although the beds are not physically moved, the material may now be described as being in a "purification zone." In this zone, the circulating bulk fluid is depleted of the preferentially adsorbed component in the feed stream. The circulating bulk fluid in the purification zone tends to dissolve and remove the unwanted components (MX, OX and EB) from the adsorbent material, e.g., from within and from the interstitial areas between the solids. Thus, a fluid comprising unwanted components, e.g., raffinate, passes through the purification zone along with the flow of the circulating bulk fluid. The unwanted components (MX, OX and EB) may be withdrawn in a raffinate stream located below the adsorption zone. Because an objective of the adsorption process is to separate the desired component (PX) from other components (MX, OX and EB), which have nearly the same boiling point or density as the desired component (PX), purification displaces unwanted components (MX, OX and EB) and substitutes another fluid (e.g., a desorbent) which can be more readily separated by other means, e.g., distilled.

Desorption Zone: After the adsorbent solids have, in a simulated manner (by virtue of changing the location of inlet and outlet streams of the adsorbent vessel), "passed through" the purification zone, the adsorbent solids enter the desorption zone. The desorption zone may comprise a plurality of adsorbent beds. A desorbent stream is introduced in one end of the desorption zone, along with the circulating bulk fluid to the adsorbent bed located furthest upstream in terms of the direction of flow of the circulating fluid through the beds of the desorption zone. The desorbent stream contains desorbent which is more preferentially adsorbed by the adsorbent solids than the product comprising the desired component (PX). The desorbent chosen will depend in part upon the desired component(s), the adsorbent materials, and the ease with which the desorbent can be separated from the product. The desorbent flows along with the circulating fluid and desorbs the desired component (PX) from the adsorbent solids. An extract stream is taken from the circulating fluid at the other end of the purification zone, which is located at the location of the adsorbent bed furthest downstream in terms of the direction of flow of the circulating fluid through the beds of the desorption zone. The extract stream may comprise the desired product (PX), desorbent and only trace or insignificant amounts of unwanted components (MX, OX and EB). Examples of desorbents include paradiethylbenzene (pDEB) and toluene (TOL).

Each and every step and zone might be present somewhere in an adsorption apparatus or system if simultaneous operations are conducted. Nevertheless, the steps may be performed successively or staggered over time. Further, in some adsorption processes, the unwanted components may be adsorbed, and the product comprising the desired component(s) allowed to pass through the adsorption apparatus or system. Therefore, in a given system, the terms raffinate and extract are relative and may depend upon the particular nature of the components being separated, the preference of the solids, and the nature of the apparatus or system.

An apparatus suitable for accomplishing the adsorption process of this invention is a simulated moving-bed adsorption apparatus. A commercial embodiment of a simulated moving-bed adsorption apparatus is used in the well-known Parex™ Process, which is used to separate C8 aromatic isomers and provide a more highly pure paraxylene (PX) from a less highly pure mixture. See by way of example U.S. Pat. Nos. 3,201,491; 3,761,533; and 4,029,717.

Such an adsorption apparatus may comprise at least one vertical column stacked with beds of adsorbent solids. The beds may be in trays packed with the adsorbent solids. One or more than one type of adsorbent solid may used. The column(s) may have the capability to perform each of the above-described steps simultaneously within different locations, e.g., zones, in the column(s). Thus, the composition of the fluid in the column(s) may vary between zones although there may be no structures completely separating these zones. A serially and circularly interconnected matrix of fluid communication conduits including associated valves, pumps, and so forth, may permit inlet and effluent streams to be directed and redirected into different zones of the column(s). The fluid communication conduits including associated valves, pumps, and so forth, may be configured to pass a variety of streams through each of the conduits. These streams may pass into the adsorbent vessel, as inlet streams, or out of the vessel as effluent streams. Over time, both inlet and effluent streams may pass through each of the individual conduits. The different zones within the chamber may have constantly shifting boundaries as the process is performed.

The circulating flow of bulk fluid through the adsorbent apparatus may be facilitated by pumping the effluent from the bottom bed of an adsorbent column and passing this effluent as an inlet stream to the top bed of another adsorbent column. When the adsorption process involves the use of more than one adsorbent columns connected in series, the effluent from the bottom bed of a first column may be passed as an inlet stream to the top bed of a second adsorbent column, and the effluent from the bottom bed of the last column in the series may be passed as an inlet stream to the top bed of the first adsorption column.

A manifold arrangement may be used to cause the adsorbent solids to flow, in a simulated manner, in a counter current manner with respect circulating bulk fluid. The valves in the manifold may be operated in a sequential manner to effect the shifting of inlet and outlet streams. In this regard, see U.S. Pat. No. 3,706,812. Another means for producing a simulated countercurrent flow of the solid adsorbent is a rotating disc valve by which inlet and outlet streams, e.g., feed, extract, desorbent, raffinate, and conduit flush, are cyclically changed during the course of the process. Both U.S. Pat. Nos. 3,040,777 and 3,422,848 disclose suitable rotary valves. Both suitable manifold arrangements and disc valves are known in the art. More recently, a system has been described using dual rotary valves. See U.S. Pat. No. 8,168,845.

Normally there are at least four streams (feed, desorbent, extract, and raffinate) employed in the procedure. The location at which the feed and desorbent streams enter a column of adsorbent beds and the extract and raffinate streams leave the column are simultaneously shifted in the same direction at set intervals. The direction of the shift is the same as the direction of the flow of the circulating bulk fluid through the adsorption chamber. Each shift in location of these transfer points delivers or removes liquid from a different bed within the column. In many instances, one zone may contain a larger quantity of adsorbent material than other zones. Moreover, zones other than those discussed above may also be present. For example, in some configurations, a buffer zone between the adsorption zone and the desorption zone may be present and may contain a small amount of adsorbent material relative to the zones surrounding it. Further, if a desorbent is used that can easily desorb extract from the adsorbent material, only a small amount of the material need be present in the desorption zone in comparison to the other zones. As noted above, the adsorbent need not be located in a single column, but may be located in multiple columns or a series of columns.

A plurality of fluid communication conduits may be used to introduce fluids to the beds and to withdraw fluids from the beds. The same fluid communication conduit may be used in a first instance to input a feedstream into the apparatus or system and later to withdraw an extract stream. This can result in reduced product purity due to contamination of the withdrawn product. Fluid communication conduits may contain unwanted components, such as residue remaining in the conduit from earlier additions or withdrawals of streams. This problem may be overcome by employing separate conduits for each stream or by removing such residue from the conduits by flushing them with a medium which would not affect product purity as adversely as would an unwanted component remaining in the fluid communication conduit. A preferred flushing medium has been the recycled product or the desorbent, which might be more readily separated downstream of the chamber than would the residue. See U.S. Pat. No. 4,031,156. Nevertheless, flushing conduits with the recycled product reduces the output of the adsorption process. Furthermore, the excessive use of desorbent may result in an increase in the desorbent consumption and may also desorb certain amount of sorbate adsorbed within the purification zone, thereby limiting the overall efficiency of the system.

A standard Parex™ unit for separating paraxylene (PX) from the other C8 aromatic isomers, metaxylene (MX), orthoxylene (OX), and ethylbenzene (EB), has a single feed to a rotary valve device comprising a single rotary valve or parallel rotary valves. The rotary valve device directs the feed to a conduit to adsorbent beds, which (viewed schematically, such as in the attendant drawings described herein) are located between the location of a first and second withdrawal stream. The first withdrawal stream is an extraction stream (which may comprise, by way of example, 99.7% PX, based on the amount of xylenes, and desorbent), and the second withdrawal stream is a raffinate stream (which comprises PX-depleted xylenes and desorbent). The conduits in fluid communication with the adsorption apparatus and the rotary valve(s) are shared with all of the feed and product streams, and, therefore, these lines must be flushed between the feed injection point and the extract withdrawal point in order to prevent contamination of the product. A standard unit has a first or primary flush which removes the majority of contaminants and a second or secondary flush which removes trace impurities before, preferably just before, the extract point.

The standard commercial simulated moving bed has only a single feed inlet. Various streams of different compositions may be blended together and fed to a single point in the Parex™ process. However, as indicated in U.S. Pat. No. 5,750,820 (see also U.S. Pat. No. 7,396,973), feeds, which are of substantially different composition, may be segregated from one another. For example, a feed, which is more highly concentrated in paraxylene, may be introduced upstream (in terms of the direction of the flow of circulating fluid) from a feed, which is less concentrated in paraxylene. An example of a feed, which is more highly concentrated in paraxylene, may be obtained from a selective toluene disproportionation unit. Such units may produce C8 aromatic mixtures having, for example, 85-90% paraxylene. Examples of feeds, which are less concentrated in paraxylene, may be obtained, for example, from a powerformer, isomerization unit or transalkylation unit. These units tend to produce equilibrium xylenes. These equilibrium xylenes may comprise a mixture of xylenes having, for example, about 23% paraxylene. The units which produce and recover xylenes, also tend to recover ethylbenzene. Ethylbenzene may be included as an impurity to the feed of a unit which produces paraxylene. The amount of ethylbenzene in the product recovered along with the equilibrium xylenes varies from process to process, depending on the type of process used to generate the equilibrium xylenes. For example, the proportion of ethylbenzene in the C8 aromatics produced and recovered in a reforming process may be different from the proportion of ethylbenzene produced and recovered in a transalkylation process.

As suggested in U.S. Pat. No. 5,750,820 (see also U.S. Pat. No. 7,396,973), the primary or first line flush may be used as a second feed point for the paraxylene concentrate, and the secondary flush may be used as the primary flushing stream.

There may be a problem with the above configuration when the standard Parex™ unit has the secondary flush located close to the extract withdrawal point. When the secondary flush is very close to the extract withdrawal point and concentrated paraxylene (having associated impurities) is flushed from the conduit in fluid communication with the rotary valve and the adsorption chamber, the configuration may be such that the point of the secondary flush is too close to the extract withdrawal point and the highest separation of the feed will not be realized.

This problem is addressed in U.S. Pat. No. 8,569,564. A solution is that the feed locations of both the primary flush (including concentrated paraxylene) and the secondary flush are modified to realize the full benefit of the feed configuration in U.S. Pat. No. 5,750,820. By moving the secondary flush further away from the extract, the material flushed from the conduit will be injected at a more efficient location. See U.S. Pat. No. 8,529,757. The problem and solution addressed in U.S. Pat. No. 8,569,564 are noted in the description of FIG. 1 in U.S. Pat. No. 8,529,757.

Facilities for producing C8 aromatics (paraxylene, metaxylene, orthoxylene, and ethylbenzene) often have at least one separation unit, such as a unit for conducting the Parex Process™, to separate paraxylene from the other components of the C8 aromatics. These facilities include petroleum refineries and petrochemical processing plants. These facilities may include a variety of units for producing C8 aromatics. Examples of such units for producing C8 aromatics include a selective toluene disproportionation unit, a powerformer (a type of a reforming unit), an isomerization unit and a transalkylation unit. Some units, such as powerformers, isomerization units and transalkylation units, tend to form equilibrium mixtures of C8 aromatics, for example, having 23% paraxylene and 77% of the sum of metaxylene and orthoxylene, based on the total of paraxylene, metaxylene, orthoxylene in the mixture. Other units, such as selective toluene disproportionation units, tend to form mixtures enhanced (in concentration) in paraxylene in comparison with an equilibrium mixture of C8 aromatics. For example, a selective toluene disproportion unit may produce a C8 aromatics mixture having 85 to 90% paraxylene and 10 to 15% of the sum of metaxylene, orthoxylene, and ethylbenzene, based on the total of paraxylene, metaxylene, orthoxylene, and ethylbenzene in the mixture.

Another unit, which tends to produce enhanced paraxylene, as opposed to equilibrium xylenes, is a selective toluene alkylation unit. The process conducted in the selective toluene alkylation unit involves alkylating toluene with an alkylating agent, such as methanol, with selective alkylation catalyst. The selective alkylation catalyst promotes the mono-alkylation of toluene with a methyl group in the para position to selectively produce paraxylene in preference to other isomers of xylene (MX and OX), as well as polyalkylated product (e.g., trimethylbenzenes). Such selective alkylation may be accomplished with the use of a catalyst comprising a medium pore size zeolite, such as ZSM-5. Such medium pore size zeolites have interior pore spaces, which allow access and egress of a molecule of the shape and size of paraxylene, yet resist the access and egress of a molecule of the shape and size of metaxylene, orthoxylene, and trimethylbenzene.

Facilities for producing C8 aromatics have varying capacities for producing C8 aromatic mixtures enhanced in paraxylene, for example, from selective toluene disproportionation units. Processes described above, for example, in U.S. Pat. No. 5,750,820, use an equilibrium xylene feed stream (e.g., having 23% of paraxylene and 77% of other xylenes, plus a varying amount of ethylbenzene) and replaces a primary flush stream with an extra feed comprising enhanced paraxylene feed (e.g., from a selective toluene disproportionation units). Ideally, the facility producing C8 aromatics in such a process would have a relatively large capacity to produce C8 aromatics enhanced in paraxylene (e.g., from a selective toluene disproportionation unit). Such a facility could produce enhanced paraxylene in sufficient amounts to (1) flush equilibrium xylene, comprising substantial amounts of contaminants, including metaxylene, orthoxylene, and ethylbenzene, from a conduit and (2) provide an additional source of paraxylene as a second feed step the overall separation process.

Facilities for producing C8 aromatic do not always have the capacity to produce enough enhanced paraxylene to best accommodate the dual feed process described in U.S. Pat. No. 5,750,820. For example, certain facilities may not produce enough enhanced paraxylene to even completely flush equilibrium xylene from conduits, much less provide a second feed of additional C8 aromatics to the separation process. Furthermore, facilities with relatively large capacities for producing enhanced paraxylene could benefit from using a minimal amount of enhanced paraxylene in a first conduit flushing medium and blending the remaining enhanced paraxylene with equilibrium xylene in the feed stream to the adsorption process. By introducing at least a portion of the enhanced paraxylene at a point upstream (relative to the flow of circulating fluid) from the first flush stage, a greater number of adsorbent beds are provided between the feed point and extract point. This greater number of catalyst beds may enhance the separation of paraxylene from other C8 aromatics.

The extract stream from the separation process may comprise desorbent, the desired paraxylene product and a very small amount of one or more unwanted C8 aromatics (i.e. metaxylene, orthoxylene, and ethylbenzene). The paraxylene product may be recovered by a distillation process. An extract stream or a recovered paraxylene product stream may be used as the first or primary flush stream to remove the residue of C8 aromatic feed remaining in the conduit. A desorbent stream may also be used as such a flush stream. However, there are problems with using recovered paraxylene, extract or desorbent in the primary flush stream. Recycling a portion of recovered paraxylene or extract stream to the primary flush stage limits product recovery. Introducing desorbent into a bed at the location of the primary flush may interfere with adsorption of paraxylene on the adsorbent. Minimizing the introduction of desorbent into the adsorption zone maximizes the adsorbent's capacity utilization. Furthermore, there are equipment and energy costs associated with routing any of (1) recovered paraxylene product, (2) extract and (3) desorbent to the primary flush stage of the recovery process. Therefore, a process that minimizes the use of recycled paraxylene, extract, or desorbent as a primary flush medium is desired.

SUMMARY OF THE INVENTION

The present invention minimizes the use of recycled paraxylene, extract, or desorbent as a primary flush medium and provides a more efficient first flushing step by using enhanced paraxylene, supplemented with a non-C8 aromatic liquid, as the first flushing medium.

Paraxylene is separated from at least one multicomponent feed, which comprises paraxylene, orthoxylene, metaxylene, and ethylbenzene, by a simulated countercurrent adsorptive separation process. The process comprises steps (a), (b), and (c). Step (a) of the process comprises passing the multicomponent feed through a conduit and into a bed of adsorbent to adsorb paraxylene on the adsorbent. Step (b) comprises passing at least one first flushing medium through the conduit of step (a) to flush residue of the multicomponent feed into the adsorbent bed comprising adsorbed paraxylene obtained from step (a). Step (c) comprises passing at least one second flushing medium through the conduit of step (b) to flush residue of the first flushing medium into the adsorbent bed obtained from step (b).

The multicomponent feed of step (a) comprises a C8 aromatic mixture from 15 to 30 volume percent of paraxylene. The first flushing medium of step (b) comprises from 10 to 95 volume percent of a C8 aromatic mixture of paraxylene, orthoxylene, metaxylene, and ethylbenzene, based on the entire volume of the first (i.e. primary) flushing medium. This C8 aromatic mixture of step (b) comprises from 75 to 98 volume percent of paraxylene. The first flushing medium of step (b) may further comprise from 5 to 90 volume percent, based on the entire volume of the first (i.e. primary) flushing medium, of a non-C8 aromatic liquid, which is not a C8 aromatic and which is miscible with C8 aromatics. The second flushing medium comprises less than 1 volume percent of ethylbenzene, less than 2 volume percent of orthoxylene and less than 2 volume percent of metaxylene.

In addition to steps (a), (b), and (c), the process for separating paraxylene from a mixture of C8 aromatics may comprise additional steps (d) and (e). Step (d) comprises withdrawing an extract stream through the conduit from the adsorbent bed chamber and through the at least one rotary valve after the bed has been subjected to the first flushing step (b) and the second flushing step (c). Step (e) comprises passing a desorbent through a rotary valve and the conduit to the adsorbent bed chamber after the extract stream has been withdrawn from the adsorbent bed chamber according to step (d). The extract stream withdrawn according to step (d) may comprise at least 99.7 volume percent of paraxylene, based on the total volume of the extract stream.

BRIEF DESCRIPTION OF THE DRAWING

FIG. 1 is a schematic illustration of a simulated moving-bed adsorptive separation system.

DETAILED DESCRIPTION

The present invention minimizes, and may even eliminate, the use of recovered paraxylene, as well as extract, as a primary flush medium. The use of desorbent as a primary flush medium is also minimized. In certain embodiments, no or essentially no desorbent is introduced into an adsorbent bed during a primary flush step.

When xylenes are produced in a facility (e.g., a refinery or a petrochemical plant), which lacks the capacity to produce enough enhanced paraxylene (e.g., from a selective toluene disproportionation unit or selective toluene alkylation unit) to even fill the conduit space of a Parex™ unit, the enhanced paraxylene can still be used as a component of the primary flush medium. Desorbent may also be used as a second component the primary flush medium, rather than the sole component of this stream. By reducing the amount of desorbent in the primary flush stream with enhanced paraxylene, the amount of desorbent potentially introduced into the adsorbent bed during the primary flush stage is minimized and may even be eliminated. Even when the facility for making paraxylene includes sufficient capacity to produce enhanced paraxylene in an amount exceeding the conduit volume of the Parex™ unit, recovery of paraxylene may be enhanced by directing a portion of the enhanced paraxylene to the feed stage and another portion of the enhanced paraxylene to the primary flush stage. Equipment and energy cost saving may also be obtained by means of embodiments of the present invention.

These and other advantages will be understood by the description of embodiments of the present invention below.

Various terms used in this description will be understood in the context of this description. A further explanation of certain terms used herein is provided below.

C8 aromatics are aromatic compounds having 8 carbon atoms. Examples of C8 aromatics include paraxylene, metaxylene, orthoxylene, and ethylbenzene.

Equilibrium xylene is a mixture of C8 aromatics having a thermodynamic equilibrium concentration of the various C8 aromatic compounds when the C8 aromatics are subjected to non-selective isomerization conditions. Equilibrium xylene may be produced in a non-selective process for producing xylenes. A non-selective process for producing xylenes may involve reacting reactants over a non-selective catalyst. Equilibrium xylene may be produced, for example, in a xylene isomerization process, a transalkylation process or a reforming process. Equilibrium xylenes may also be produced by other processes. Equilibrium xylene may comprise, for example, about 23 percent paraxylene, based on the total of the xylenes.

Enhanced paraxylene is a mixture of C8 aromatics having a greater concentration of paraxylene than equilibrium xylene. Enhanced paraxylene may be produced in a selective process for producing xylenes. A selective process for producing xylenes may involve reacting reactants over a selective catalyst. Enhanced paraxylene may be produced, for example, by a selective toluene disproportion process or a selective toluene alkylation process. Enhanced paraxylene may also be produce by other processes. Enhanced paraxylene may have a concentration of, for example, at least 75% paraxylene, based on the total of C8 aromatics.

A non-selective process for producing xylenes is a process which produces equilibrium xylenes. A non-selective process for producing xylenes may take place over a non-selective catalyst. Examples, of non-selective catalysts include large pore zeolites, such as zeolite X and zeolite Y, or amorphous aluminosilicates. When toluene is disproportionated over a large pore sixe zeolite, equilibrium zeolites may be produced.

A selective process for producing paraxylene (PX) is a process which produces paraxylene in preference to other xylene isomers (MX and OX). A selective process for producing paraxylene may be produced, for example, by catalytic process over a paraxylene selective catalyst. Examples of paraxylene selective catalysts include medium pore size zeolites, such as ZSM-5, modified with selectivating agents. Selectivating agents may neutralize surface catalytic sites or narrow the pores of the catalyst. Examples of paraxylene selective catalysts and selectivating agents are provided by in U.S. Pat. No. 5,365,004, International Publication No. WO2013/330093, and U.S. Pat. No. 4,088,706.

Circulating bulk fluid is the fluid (i.e. liquid) which flows in a continuous manner through a simulated moving-bed adsorption apparatus. The concentration of compounds in this circulating bulk fluid changes as this fluid flows through the apparatus due to, inter alia, adsorption and desorption of xylenes, ethylbenzene and desorbent, withdrawal of fluids in extract and reformate streams, and introduction of fluids through feed, desorbent and flush streams.

A rotary valve device is a device comprising at least one rotary valve. The rotary valve device may comprise various control and accessory means, such as inlet lines, outlet lines and valves associated therewith. The rotary valve device may comprise a manifold arrangement of devices to cause the adsorbent solids to flow, in a simulated manner, in a countercurrent manner with respect circulating bulk fluid.

A simulated moving-bed adsorption apparatus is an apparatus including beds of adsorbent stacked in at least one column. In operative use of the adsorption apparatus, the beds are connected in a fluid and circular manner in series with one another.

A simulated countercurrent adsorptive separation is a separation which takes place in a simulated moving-bed adsorption apparatus.

An adsorbent column is an apparatus having adsorbent beds stacked one on top of the other.

An adsorbent bed chamber is a chamber in an adsorption apparatus containing a bed of adsorbent (i.e. adsorbent bed).

An adsorbent bed is a bed of adsorbent contained within an adsorbent bed chamber. An adsorbent column includes multiple adsorbent beds. An adsorbent apparatus has one or more adsorbent columns. Any fluid in an adsorbent bed chamber, whether or not adsorbed on an adsorbent, is considered to be part of the bed. Accordingly, when fluid is introduced into or withdrawn from an adsorbent bed chamber, the fluid is considered as being introduced or withdrawn into or from the bed, itself.

An adsorbent is a solid material, which selectively adsorbs desorbent in preference to paraxylene and which selectively adsorbs paraxylene in preference to metaxylene, orthoxylene, and ethylbenzene. In a simulated moving-bed apparatus, such as a Parex™ unit, examples of adsorbents include charcoal, ion-exchange resins, silica gel, activated carbon, zeolitic material, and the like. An adsorbent, which is particularly useful for separating paraxylene from other C8 aromatics, is a faujasite-type molecular sieve material, such as zeolite X or zeolite Y, optionally, substituted or treated with an enhancing agent, such as a Group I or II element, such as potassium or barium. Examples of adsorbents for separating paraxylene from other C8 aromatics are described in U.S. Pat. No. 3,761,533.

A sorbate is a compound, which is adsorbed on an adsorbent or desorbed from an adsorbent. In a Parex™ process for separating paraxylene from C8 aromatic mixtures, sorbates include xylenes, ethylbenzene and desorbents.

Sorbate affinity is the tendency of a sorbate, such as a paraxylene, to be adsorbed by an adsorbent. In a paraxylene separation process, paraxylene has a greater sorbate affinity to the adsorbent than other C8 aromatics. Also, ethylbenzene may have a greater sorbate affinity to the adsorbent than either metaxylene or orthoxylene.

Adsorbent selectivity is the tendency of an adsorbent to adsorb a particular sorbate from a mixture of sorbates. In a paraxylene separation process, the adsorbent will adsorb paraxylene at a faster rate than other C8 aromatics. The adsorbent may also adsorb ethylbenzene at a faster rate than either metaxylene or orthoxylene.

A desorbent is a liquid, which is equally or slightly more preferentially adsorbed on the adsorbent than paraxylene. The desorbent may have a greater sorbate affinity for the adsorbent than other C8 aromatics. The desorbent should have a boiling point significantly different than the boiling points of C8 aromatics, such that the desorbent may be separated from C8 aromatics by distillation. Examples of desorbents for a paraxylene separation process include paradiethylbenzene and toluene.

Unless otherwise specified herein, the terms, downstream and upstream, refer to the direction of flow of circulating bulk fluid.

A number of abbreviations are used herein. PX stands for paraxylene. MX stands for metaxylene. OX stands for orthoxylene. EB stands for ethylbenzene. pDEB stands for paradiethylbenzene. TOL stands for toluene. NA stands for non-aromatics. Non-aromatics, such as paraffins, may be introduced into an adsorption apparatus as a feed impurity, especially when the feed comprises C8 aromatics obtained from a reforming process.

In a Parex™ unit, the locations of liquid input and output are moved by a fluid directing device described herein as a rotary valve device. This device may comprise one or more rotary valves, as well as various control and accessory means, such as inlet lines, outlets lines and valves associated therewith. The rotary valve device works in conjunction with conduits located between the adsorbent beds. The rotary valve device accomplishes moving the input and output locations through first directing the liquid introduction or withdrawal lines to specific conduits in fluid communication with particular adsorbent beds. After a specified time period, called the step time, the rotary valve device advances one index and redirects the liquid inputs and outputs to the conduit immediately adjacent and downstream of the previously used conduits. Each advancement of the rotary valve device to a new position is generally called a valve step, and the completion of all the valve steps is called a valve cycle. The step time is uniform for each valve step in a valve cycle, and may be from about 60 to about 90 seconds (although it can be longer or shorter).

An example of a simulated moving bed adsorption apparatus contains 24 adsorbent beds, 24 conduits individually connected to a bed and providing fluid communication with the rotary valve device. The conduits of the adsorption apparatus may function, over time, as at least two liquid input lines (e.g., a feed input line and a desorbent input line) and two liquid output lines (e.g., an extract withdrawal line and a reformate withdrawal line).

As described more fully in U.S. Pat. No. 8,529,757, a system employing a simulated countercurrent flow process such as described in U.S. Pat. Nos. 3,201,491; 3,761,533; and 4,029,717, are shown in FIG. 1, along with several modifications. The diagram in FIG. 1 will be understood by those of skill in the art to depict a simulated moving-bed process. Desorbent is introduced through conduit 100. Liquid withdrawal stream leaves the apparatus through conduit 101. Extract (containing the desired product) leaves the apparatus via conduit 102. Raffinate leaves the apparatus through conduit 110. The secondary flush is added through conduit 103. The primary flush is added through conduit 106. A C8 aromatic feed, which comprises 15 to 30 volume percent paraxylene, is added to the apparatus through conduit 107. Optionally, a C8 aromatic mixture, which comprises 75 to 98 volume percent paraxylene, is added as an additional feed through conduit 108. Optionally, a C8 aromatic mixture, which comprises 80 to 95 volume percent paraxylene is added as a portion of the primary flushing medium through conduit 109 as explained more fully in the following description.

Not shown in the drawing, but as would be recognized by one of skill in the art in possession of the disclosure of U.S. Pat. No. 8,529,757, is one or more distillation towers and attendant pumps and conduits, which may be utilized to purify the liquid withdrawal stream leaving the above-described apparatus via conduit 101. However, such downstream operations can be minimized or entirely omitted by rerouting (such as by replumbing or retrofitting) the liquid withdrawal stream from conduit 101 to conduit 103. In this way, the liquid withdrawal stream from conduit 101 is used as the secondary flush medium, which is introduced into the apparatus through conduit 103.

Continuing with the description of FIG. 1, the arrow 112 represents the simulated movement of beds upward through apparatus 120 containing plural adsorption bed chambers $A_1$ through $A_{n+j}$. Arrow 111 represents the countercurrent flow of circulating bulk fluid to the adsorbent beds. In operation, the adsorbent does not flow, but the various inlet and outlet streams, such as feed, product and flush streams, cycle through the adsorbent bed chambers, represented by lines $A_1$ through $A_{n+j}$, in a direction, which is countercurrent to the simulated movement of adsorbent beds and cocurrent to the direction of the circulating bulk fluid. This simulates the movement of the adsorbent beds $A_1$ through $A_{n+j}$. Theoretically, there may be any number of adsorbent beds, thus n>2 and n+j is the maximum number of adsorbent beds. However, from a practical standpoint the number of bed lines is limited by design considerations and other factors. It will be understood that n and j are positive integers and that in an example of a commercial embodiment the total number of adsorbent beds is 24, and thus n+j typically may be 24. Certain adsorbent beds, i.e., beds between $A_2$ and $A_n$, beds $A_{n+3}$, $A_{n+5}$, $A_{n+6}$, and $A_{n+10}$ through $A_{n+j-1}$ are not depicted in FIG. 1, for convenience of view.

In the unit shown in FIG. 1, xylene and ethylbenzene molecules from feed 107 are adsorbed in bed $A_{n+9}$. As the adsorbent in bed $A_{n+9}$ becomes saturated with C8 aromatics, a portion of the C8 aromatics in the feed flow along with circulating bulk fluid and flow into at least one bed, such as $A_{n+10}$ (not shown in FIG. 1), below bed $A_{n+9}$. According to a predetermined cycle time, the flow of feed, along with the flows of other inlet and outlet streams, is shifted to one adsorbent bed below. In FIG. 1 the bed below $A_{n+9}$ would be bed $A_{n+10}$ (not shown in FIG. 1). The direction of the shifting of feed and other streams to and from the adsorbent apparatus is the same as the direction of the flow of the circulating bulk fluid through the apparatus. This shifting of streams results in adsorbed C8 aromatics being moved (in a simulated manner) to beds above the bed to which feed is being introduced at any given time.

The feed which is introduced through conduit 107 may comprise equilibrium xylenes (such as from a powerformer, isomerization unit or transalkylation unit). Such equilibrium xylenes may comprise about 21-24 wt % paraxylene (PX). A portion of the feed introduced through conduit 107, may also comprise enhanced paraxylene, for example, from a selective toluene disproportionation unit (STDP unit). This enhanced paraxylene may comprise, for example, about 85-90 wt % PX. In one embodiment, the feed introduced through conduit 107 is free of enhanced paraxylene from a toluene disproportional process.

The paraxylene is desorbed from adsorbent in the beds by desorbent, which is introduced into bed $A_1$ of the adsorption apparatus through conduit 100. The desorbent has a stronger binding affinity to the adsorbent than any of the C8 aromatics. The desorbent also has a different boiling point than the C8 aromatics and is easily separated from C8 aromatics in a distillation process. Examples of desorbents include paradiethylbenzene (pDEB), toluene (TOL), or a mixture thereof, or some other strongly adsorbed compound. The stream, which is introduced into the apparatus through conduit 100, may, optionally, also comprise a diluent, such as a non-aromatic (NA) hydrocarbon, which has less binding affinity to the adsorbent than any of the C8 aromatics. However, such diluents take up volume in the apparatus and are not necessary. Accordingly the stream, which is introduced into the apparatus through conduit 100, is preferably free of such diluent.

An extract stream is withdrawn from bed $A_n$ through conduit 102. The extract stream comprises a mixture of the purified paraxylene and the desorbent. As shown in FIG. 1, the withdrawal point of the extract stream though conduit 102 is between the point of introduction of the feed through conduit 107 and the point of introduction of the desorbent through conduit 100. A raffinate stream is withdrawn from bed An+j through conduit 110. The raffinate stream comprises paraxylene-depleted C8 aromatics and desorbent.

In view of the configuration of the simulated moving-bed process, the various feeds and products must share the conduits between the adsorbent beds and the rotary valve device (not shown). To prevent contamination of the extract stream with residual metaxylene, orthoxylene, and ethylbenzene from the residue of feed stream in the conduit, the conduit is flushed in two stages with first a primary medium and second with a secondary flush medium. Liquid which is optionally withdrawn through conduit 101 may either be sent to the extract tower for recovery or recycled and used for primary flush through conduit 106 or secondary flush through conduit 104.

A first or primary flushing medium is introduced into conduit 106, including a terminal portion 114 of this conduit, which is connected to adsorbent apparatus 120. In FIG. 1, the primary flush fluid displaces residual feed in the conduit at the location of bed $A_{n+7}$, which is two beds above (i.e. two beds upstream, in terms of the direction of circulating bulk fluid) bed $A_{n+9}$ into which feed is introduced via conduit 107. Although not shown in FIG. 1, it will be understood that conduit 106 may be connected to beds located further away, e.g., bed $A_{n+6}$, or closer, e.g., bed $A_{n+8}$, than bed $A_{n+7}$. The primary flushing medium comprises at least two components, e.g., a non-C8 aromatic, such as desorbent and a C8 aromatics mixture, comprising, for example, from 80 to 95 volume percent paraxylene. These components may be mixed upstream of a rotary valve device (not shown in FIG. 1) and passed together through the rotary valve device into conduit 106. In another embodiment, these components may be passed sequentially into conduit 106. For example, the C8 aromatics mixture, comprising from 80 to 95 volume percent paraxylene, may be passed first through a rotary valve device into conduit 106, followed by passing desorbent component through the rotary valve device and into conduit 106. In another embodiment, at least a portion of the C8 aromatics mixture, comprising from 80 to 95 volume percent paraxylene, may be passed directly to the terminal portion 114 of conduit 106 through conduit 109. A portion of the C8 aromatics mixture, comprising from 80 to 95 volume percent paraxylene, may also be introduced into a terminal portion 113 of conduit 107 via conduit 108 and introduced as feed to bed $A_{n-9}$. In another embodiment at least a portion of the C8 aromatics mixture, comprising from 80 to 95 volume percent paraxylene, may be combined with a different C8 aromatics mixture, comprising from 15 to 30 volume percent paraxylene, and this combined C8 aromatic mixture may be passed through a rotary valve device (not shown in FIG. 1) into conduit 107.

As shown in FIG. 1, a second or secondary flushing medium is introduced into conduit 103, including a terminal portion 104 of this conduit, which is connected to adsorbent apparatus 120. In FIG. 1, the secondary flush fluid displaces residual primary flush fluid in the conduit at the location of bed $A_{n+1}$, which is six beds above (i.e. six beds upstream, in terms of the direction of circulating bulk fluid) bed $A_{n+7}$ into which primary flush fluid is introduced and one bed below bed $A_n$ from which an extract stream is withdrawn via conduit 102. However, it will be understood that the flow of secondary flush fluid through conduit 103 may be diverted to a bed located further away from bed $A_n$ and closer to bed $A_{n+7}$. In FIG. 1, this diversion of flow is shown by conduit 105, which is connected to bed $A_{n+4}$. When the secondary flush medium comprises little or no metaxylene, orthoxylene, and ethylbenzene, the secondary flush medium and the residue of primary flush medium in the conduit comprises little or no metaxylene, orthoxylene, and ethylbenzene, the secondary flush medium may flow towards a bed located close (e.g., one bed away) to the extract withdrawal point. When the secondary flushing medium and the residue of the primary flushing medium in the conduit are such that significant quantities of metaxylene, orthoxylene, and especially ethylbenzene are introduced, the bed, to which the secondary flushing medium is directed, the location of the secondary flush step should be further away from the extract point to allow sufficient separation of paraxylene from the other C8 aromatics.

Again, it should be emphasized, as would be known by one of skill in the art, that these positions are relative and that, although the actual positions change by virtue of the movement of the rotary valve (not shown), the relative positions of the conduits remains the same. Thus, it will be understood by one of ordinary skill in the art that FIG. 1 depicts a simplified simulated moving-bed apparatus with a rotary valve, wherein countercurrent "movement" of the solids in beds $A_1$ through $A_{n+j}$ relative to the fluid streams is simulated by the use of the rotary valve, which is not shown in the FIG. 1. As the valve rotates, the zones previously discussed move through the column in a stepwise sequence due to the change in the stream flows through the valve. In embodiments, a preferred rotary valve for performing this invention is described in U.S. Pat. No. 3,205,166. In this arrangement, each fluid communication conduit connected to the chamber may serve a different function with each step rotation of the rotary valve.

Paraxylene is separated from at least one multicomponent feed, which comprises paraxylene, orthoxylene, metaxylene, and ethylbenzene, by a simulated countercurrent adsorptive separation process performed in a system like that described above and represented in FIG. 1. The process comprises steps (a), (b) and (c).

Step (a) of the process comprises passing the multicomponent feed through a conduit and into a bed of adsorbent to adsorb paraxylene on the adsorbent. Step (b) comprises passing at least one first flushing medium through the conduit of step (a) to flush residue of the multicomponent feed into the adsorbent bed comprising adsorbed paraxylene obtained from step (a). Step (c) comprises passing at least one second flushing medium through the conduit of step (b) to flush residue of the first flushing medium into the adsorbent bed obtained from step (b).

The multicomponent feed of step (a) comprises a C8 aromatic mixture of paraxylene, orthoxylene, metaxylene, and ethylbenzene. This C8 aromatic mixture of step (a) further comprises from 15 to 30 volume percent, for example, from 15 to 27 volume percent, for example, from 21 to 24 volume percent, paraxylene. Thus, the remainder of the multicomponent feed of step (a) comprises from 70 to 85 volume percent, for example, from 70 to 80 volume percent of the sum of orthoxylene, metaxylene, and ethylbenzene.

The first flushing medium of step (b) comprises from 10 to 95 volume percent, for example, from 30 to 95 volume percent, for example, from 30 to 80 volume percent, of a C8 aromatic mixture of paraxylene, orthoxylene, metaxylene, and ethylbenzene, based on the entire volume of the first (i.e. primary) flushing medium. This C8 aromatic mixture of step (b) comprises from 75 to 98 volume percent, for example, from 75 to 95 volume percent, for example, from 78 to 95 volume percent, for example, from 78 to 93 volume percent, for example, from 85 to 93 volume percent, of paraxylene.

The first flushing medium of step (b) further comprises from 5 to 90 volume percent, for example, from 10 to 90 volume percent, for example, from 10 to 70 volume percent, for example, from 20 to 70 volume percent, based on the entire volume of the first (i.e. primary) flushing medium, of a non-C8 aromatic liquid, which is not a C8 aromatic and which is miscible with C8 aromatics. The volume of the non-C8 aromatic mixture, which is introduced into the conduit during step (b), may be from 30 to 200 percent, for example, from 30 to 150 percent, for example, from 30 to 100 percent, for example, from 30 to 50 percent, of the volume of the conduit.

According to one embodiment, C8 aromatics and non-C8 aromatics may be introduced into the conduit together during the first flushing step (b). According to another embodiment, C8 aromatics and non-C8 aromatics may be introduced into the conduit sequentially. For example, the first flushing step of step (b) may comprise sequentially passing into the conduit the C8 aromatic mixture, followed by passing the non-C8 aromatic into the conduit.

The non-C8 aromatic of step (b) may comprise at least one unsubstituted hydrocarbon. Examples of such hydrocarbons include paradiethylbenzene, toluene, tetralin (i.e. tetrahydronaphthalene), cyclohexane and paraffins having from 6 to 20 carbon atoms. The non-C8 aromatic of step (b) may also comprise at least one substituted hydrocarbon, such as dimethylsulfoxide or tetrahydrofuran. A particular non-C8 aromatic is paradiethylbenzene.

When the primary flush step (b) is conducted in a sequential manner, such that enhanced paraxylene is first introduced into a conduit followed by introduction of a non-C8 aromatic liquid in an amount sufficient to substantially displace the residue of enhanced paraxylene out of the conduit, a second or secondary flush step may be omitted.

The second flushing medium of step (c) comprises less than 1 volume percent of ethylbenzene, less than 2 volume percent of orthoxylene and less than 2 volume percent of metaxylene. For example, the second flushing medium may comprise less than 1.0 volume percent of the sum of paraxylene, orthoxylene, metaxylene, and ethylbenzene. Examples of second flushing mediums include desorbent, recovered paraxylene, extract, fluid taken from an adsorbent bed in the purification zone at a point between the point of the withdrawal of the extract stream and the point of the introduction of the desorbent stream, a non-C8 aromatic liquid, and mixtures thereof. The second flushing medium of step (c) may also comprise at least one unsubstituted hydrocarbon. Examples of such hydrocarbons include paradiethylbenzene, toluene, tetralin, cyclohexane, and paraffins having from 6 to 20 carbon atoms.

In addition to steps (a), (b), and (c), the process for separating paraxylene from a mixture of C8 aromatics may comprise additional steps. For example, this process may further comprise steps (d) and (e). Step (d) comprises withdrawing an extract stream through the conduit from the adsorbent bed chamber and through the at least one rotary valve after the bed has been subjected to the first flushing step (b) and the second flushing step (c). Step (e) comprises passing a desorbent through a rotary valve and the conduit to the adsorbent bed chamber after the extract stream has been withdrawn from the adsorbent bed chamber according to step (d). The desorbent may comprise, for example, paradiethylbenzene, toluene or tetralin. A tetralin desorbent is described in U.S. Pat. No. 8,283,274. The first flushing medium may comprise from 5 to 90 volume percent, for example, from 5 to 70 volume percent, for example, from 20 to 70 volume percent, based on the total volume of the first flushing medium, of the desorbent used in step (e). The second flushing medium of step (c) may comprise at least 99 volume percent, based on the total volume of the second flushing medium, of the desorbent used in step (e).

The separation process may also comprise a step (f), which comprises withdrawing a portion of the liquid from the adsorbent bed chamber through the conduit and a rotary valve before desorbent has been passed through the conduit into the adsorbent bed chamber according to step (e) and after a liquid stream has been removed from said chamber through the conduit according to step (d). According to one embodiment, at least of a portion of the liquid withdrawn according to step (f) is used as at least a portion of the second flushing medium of step (c). According to another embodiment, at least of a portion of the liquid withdrawn according to step (f) is used as at least a portion of non-C8 aromatics in step (b).

The simulated countercurrent adsorptive separation may take place in an apparatus comprising multiple adsorbent bed chambers. The adsorbent bed chambers may each comprise beds of adsorbent stacked one on top of the other. A circulating bulk fluid may flow in a continuous manner into the top of an adsorbent bed chamber, through the adsorbent bed and down to the top of the next adsorbent bed chamber. Separate conduits may provide fluid communication between each adsorbent bed chamber and the at least one rotary valve.

The flow of liquids through conduits to and from adsorbent bed chambers may be controlled by the rotary valve, such that, over time, each of steps (a), (b), (c), (d), (e), and (f) take place in each of the adsorbent bed chambers of the apparatus. The apparatus comprising multiple adsorbent bed chambers may comprise from 10 to 50, for example, from 16 to 32, for example 24, adsorbent bed chambers.

At the same time that the multicomponent feed is passed through a rotary valve through a first conduit into an adsorbent bed in a first adsorbent bed chamber according to step (a), steps analogous to steps (b), (c), (d), (e), and (f) may occur in other chambers and conduits of the adsorption apparatus. An example of a step, which is analogous to step (b), is step (b'). Step (b') may comprise passing the at least one first flushing medium through a rotary valve and then into a second conduit in fluid communication with a second adsorbent bed chamber to flush residue of multicomponent feed from the second conduit and into the adsorbent bed of the second adsorbent bed chamber. The second adsorbent bed chamber is located upstream from the first adsorbent bed chamber, based on direction of the flow of circulating bulk fluid.

An example of a step, which is analogous to step (c), is step (c'). Step (c') takes place only if step (c) takes place. If step (c) is omitted, then step (c') is also omitted. Step (c') may comprise passing the at least one second flushing medium through a rotary valve and then into a third conduit in fluid communication with a third adsorbent bed chamber to flush residue of the first flushing medium in the third conduit into the adsorbent bed of the third adsorbent bed chamber. The third adsorbent bed chamber is located upstream from the second adsorbent bed chamber, based on direction of the flow of circulating bulk fluid.

An example of a step, which is analogous to step (d), is step (d'). Step (d') may comprise passing an extract stream through a fourth conduit and then into a rotary valve, wherein the fourth conduit is in fluid communication with a fourth adsorbent bed chamber. The fourth adsorbent bed chamber is located upstream from the third adsorbent bed chamber, based on direction of the flow of circulating bulk fluid.

An example of a step, which is analogous to step (e), is step (e'). Step (e') may comprise passing the desorbent through a rotary valve and then into a fifth conduit in fluid communication with a fifth adsorbent bed chamber. The fifth adsorbent bed chamber is located upstream from the fourth adsorbent bed chamber, based on direction of the flow of circulating bulk fluid.

An example of a step, which is analogous to step (f), is step (f'). Step (f') may comprise withdrawing a liquid from a sixth adsorbent bed chamber into a sixth conduit and then through a rotary valve. The sixth adsorbent bed chamber may be upstream from fourth adsorbent bed chamber and downstream from the fifth adsorbent bed chamber, based on direction of the flow of circulating bulk fluid. At least a portion of the liquid withdrawn according to step (f') may be used as at least a portion of the at least one second flushing medium.

At least one adsorbent bed chamber may be located upstream, based on the direction of the flow of circulating bulk fluid, from the adsorbent bed chamber into which the first flushing medium is introduced according to step (b') and downstream, based on the direction of the flow of circulating bulk fluid, from the adsorbent bed chamber into which the secondary flushing medium is introduced according to step (c'). Also, at least one adsorbent bed chamber may be located upstream, based on the direction of the flow of circulating bulk fluid, from the adsorbent bed chamber from which extract fluid is withdrawn according to step (d') and downstream, based on the direction of the flow of circulating bulk fluid, from the adsorbent bed chamber from which liquid is withdrawn according to step (f').

The extract stream withdrawn according to step (d) may comprise at least 99.7 volume percent of paraxylene, based on the total volume of xylenes and ethylbenzene present in the extract stream.

According to one embodiment, at least 50 volume percent of the C8 aromatic mixture, which provides a multicomponent feed, may be produced by at least one refinery or petrochemical process. This C8 aromatic mixture in the feed, which is produced by at least one refinery or petrochemical process, may comprise from 15 to 30 volume percent, for example, from 20 to 30 volume percent of paraxylene.

The first flushing medium of step (b) may comprise from 10 to 95 volume percent, for example, from 30 to 95 volume percent, for example, from 30 to 90 volume percent, of a C8 aromatic mixture of paraxylene, orthoxylene, metaxylene, and ethylbenzene. This C8 aromatic mixture, which is part of the first flushing fluid of step (b), may be produced by at least one refinery or petrochemical process. This C8 aromatic mixture, which is part of the first flushing fluid of step (b), may comprise from 75 to 98 volume percent, for example, from 78 to 95 volume percent, for example, from 80 to 95 volume percent, of paraxylene.

Examples of refinery or petrochemical processes for producing the at least 50 volume percent of the C8 aromatic mixture in the multicomponent feed of step (a), which mixture comprises from 15 to 30 volume percent of paraxylene, include a reforming process, an isomerization process, a transalkylation process and a mixture of any of these processes.

An example of a refinery or petrochemical process for producing the at least 50 volume percent of the C8 aromatic mixture, which is part of the first flushing medium of step (b), which mixture comprises from 75 to 98 volume percent of paraxylene, is a selective toluene disproportionation process. Other examples of refinery processes for producing enhanced paraxylene are discussed hereinafter.

In the description of the separation process, certain steps (e.g., steps (a)-(f)) are described, primarily, from the perspective of what happens over time in an individual bed and conduit connected thereto in a simulated moving-bed adsorption apparatus containing 24 beds. These steps are also described, primarily, in terms of what happens at a steady state operation of the adsorption process. The process achieves a steady state of operation after a start-up stage, which is described in more detail hereinafter.

For example, in a steady state operation of the process, the first stage of process involves introducing a feed through a conduit and into a bed, as per step (a). As feed is introduced, the concentration of fluid in the bed chamber becomes concentrated in C8 aromatics. Eventually, the concentration of C8 aromatics becomes sufficient to displace adsorbed desorbent from the bed and C8 aromatics are adsorbed on the bed. As the flow of feed continues, a portion of the C8 aromatics may become entrained in the circulating bulk fluid, and C8 aromatics become adsorbed in the adsorbent in one or more beds downstream, in terms of the direction of the flow of the circulating bulk fluid, of the bed to which feed is being introduced. Over time, the flow of feed to the bed of step (a) is discontinued, and the flow of feed is shifted to the next bed downstream, in terms of the direction of the flow of the circulating bulk fluid, of the bed of step (a).

Each time that the flow of feed is shifted to a downstream bed, a bed comprising adsorbed xylenes is, effectively, in a simulated manner, moved or pushed upstream, in terms of the flow of circulating bulk fluid, in the series of beds. Over time, the beds furthest upstream become enhanced in the concentration of paraxylene and depleted in metaxylene, orthoxylene, and ethylbenzene. Also, beds further downstream from the feed location become enhanced in the concentration of metaxylene, orthoxylene, and ethylbenzene and depleted in paraxylene.

After the flow of feed to the bed of step (a) is discontinued, the conduit connected to this bed remains filled with the feed. This residual feed is flushed out of the conduit before an extract stream is taken out of the bed and is passed through the conduit. According to step (b), a first flush (i.e. a primary flush) is accomplished by displacing residual feed in the conduit with a first flushing medium comprising an enhanced paraxylene. This first flushing step may take place when the flow of the feed stream has been shifted one, two or three beds downstream, in terms of the direction of the flow of the circulating bulk fluid. After the flow of primary flushing medium, according to step (b), is discontinued, the flow of primary flushing medium may be shifted to the conduit connected to the bed immediately downstream, in terms of the direction of the flow of the circulating bulk fluid. The downstream shifting of the flow of first flushing medium into beds may take place simultaneously with the downstream shifting of the flow of feed into the beds.

The residue of the first flushing medium, introduced into the conduit in step (b), to the extent that it includes an enhanced paraxylene component, still contains some unwanted C8 aromatics other than paraxylene. Residue of these unwanted C8 aromatics may be flushed or displaced from the conduit in a second or secondary flush step (c).

According to step (c), a second flush (i.e. a secondary flush) is accomplished by displacing residual first flushing medium in the conduit with a second flushing medium comprising, at most, a very small amount of metaxylene, or orthoxylene, or ethylbenzene. This second flushing step (c) may take place when the first flushing stream has been shifted, for example, at least three beds downstream, in terms of the direction of the flow of the circulating bulk fluid. The downstream shifting of the flow of secondary flushing medium into beds may take place simultaneously with the downstream shifting of the flow of feed and first flushing medium into the beds.

When the flow of the second flushing medium is discontinued, the liquid in the conduit, which contained a considerable amount of C8 aromatics other than paraxylene immediately after the feed step (a), will now contain a considerably less C8 aromatics other than paraxylene. The conduit will now be sufficiently flushed to conduct extract step (d) without contaminating the withdrawn extract with a liquid residue in the conduit containing significant quantities of C8 aromatics other than paraxylene.

The extract step (d) may take place when the flow of secondary flushing medium has been shifted, for example, by at least 1 bed downstream. When the secondary flushing medium is free or essentially free of C8 aromatics, the location of the introduction may be located in close proximity, e.g., only one bed or two beds downstream, from the bed from which extract is being withdrawn. When the secondary flush stream includes greater amounts of C8 aromatics, which are not paraxylene, the introduction of the secondary flush stream may be, more desirably, located further away from the location of the extract stream. For example, when the secondary flush medium comprises even small quantities, e.g., 1 volume percent or less, of metaxylene, or orthoxylene or, especially, ethylbenzene, a number of intervening beds between the secondary flush point and the extract point serve to allow circulating bulk fluid to desorb C8 aromatics, which are not paraxylene, before an extract stream is withdrawn. The presence of ethylbenzene in the secondary flush stream is problematic in that ethylbenzene has a greater adsorption affinity to most adsorbents for xylene separation processes than both metaxylene and orthoxylene. For example, the adsorption affinity of paraxylene may be about twice the adsorbent affinity of ethylbenzene and the adsorption affinity of ethylbenzene may be about twice the adsorption affinity of metaxylene and orthoxylene. When the secondary flush medium contains C8 aromatics in a concentration in excess of that desired in the conduit during the extract step (d), the location of the flow of the secondary flush medium may be, for example, 3 or 4 beds downstream of the location of the bed from which the extract stream is withdrawn. An example of such a downstream location of the secondary flush stream is described in U.S. Pat. No. 8,569,564.

In order to provide an extract stream composed of desorbent and paraxylene with minimal quantities of metaxylene, orthoxylene, and ethylbenzene, a desorbent stream is introduced, according to step (e), to a bed at a location upstream, in terms of the direction of the flow of circulating bulk fluid, from location of the bed, from which an extract stream is withdrawn. The desorbent stream may be introduced, for example, at a location at least 3 beds upstream from the location of the bed, from which extract is withdrawn.

Liquid from a bed downstream from the bed to which a desorbent stream is introduced may be used as a secondary flush medium. In particular, this liquid includes very little, if any, metaxylene, orthoxylene, and ethylbenzene. Accordingly, in one embodiment of the overall separation process, a stream of liquid is withdrawn, according to step (f), downstream, for example, one bed downstream, from the location of the bed to which a desorbent stream is introduced, and this withdrawn liquid is reintroduced into the adsorption apparatus as the secondary flush stream. According to another embodiment, at least a portion of the stream withdrawn in step (f) may also be used as a source of non-C8 aromatic liquid in the primary flush step (b).

A raffinate stream is withdrawn downstream from the location of the introduction of the feed stream. The location of the bed from which the raffinate stream is withdrawn may be, for example, at least 5 beds downstream, in terms of the direction of the flow for the circulating bulk fluid, from the location of the feed stream.

In the space between the location of the introduction of the feed stream and the withdrawal of the raffinate stream, there is a gradient of concentration of C8 aromatics. For example, the adsorption chamber, to which feed is introduced, builds up a considerable amount of paraxylene from the feed. As this liquid passes as circulating bulk fluid to beds downstream of the feed chamber, the liquid becomes increasingly depleted in paraxylene and more enriched in other C8 aromatics (e.g., metaxylene, orthoxylene, and ethylbenzene). By the time this flow of circulating bulk fluid reaches the location of the bed from which the raffinate stream is withdrawn, the liquid comprises desorbent, C8 aromatics other than paraxylene, and no or essentially no paraxylene. The withdrawn raffinate stream may be distilled to remove desorbent, and the recovered C8 aromatics may be passed to an isomerization unit to produce more feed to the adsorption separation process.

The adsorption process comprising steps (a)-(f) describes, inter alia, what occurs over time in individual beds of an overall, multi-bed adsorption apparatus. It is also possible to describe this process in terms of what occurs in at a single point of time in multiple beds of the overall, multi-bed adsorption apparatus. The process for making paraxylene, summarized below, describes making a mixture of C8 aromatics, followed by an adsorption process. The adsorption process in this process for making paraxylene is described in terms of what occurs in at a single point of time in multiple beds of the overall, multi-bed adsorption apparatus.

In a process for making paraxylene, mixtures of C8 aromatics are formed in at least two steps. In one step, i.e. step (i), a first mixture of C8 aromatics is formed by at least one non-selective process to produce equilibrium xylene. For example, in step (i), C8 aromatics may be formed by a non-selective process, such as a reforming process, a transalkylation process, an isomerization process, and one or more other non-selective processes. The mixture of C8 aromatics produced in step (i) may comprise from 15 to 30 volume percent of paraxylene.

In another step, i.e. step (ii), a second mixture of C8 aromatics is formed by a selective process to produce enhanced paraxylene. Non-limiting examples of these processes include a selective toluene disproportion process (STDP), a selective toluene alkylation process, where methanol is used as the alkylating agent, a selective benzene alkylation process, where methanol is used as the alkylating agent, and a selective methanol conversion process, where methanol is converted to xylenes. These processes may be conducted in the presence of a shape selective molecular sieve catalyst. The molecular sieve may be a zeolite, for example, a medium pore size zeolite, such as ZSM-5. The molecular sieve may be treated with one or more selectivating agents, such as phosphorus or magnesium compounds, to increase the shape selectivity of the catalyst. Examples of processes for selective toluene disproportionation are described in U.S. Pat. No. 5,365,004. Examples of processes for selective toluene alkylation with a methanol alkylating agent are described in International Publication No. WO2013/330093. Examples of processes for the selective conversion of methanol to paraxylene are described in U.S. Pat. No. 4,088,706. The selective toluene alkylation process may involve replacing at least a portion of toluene reactant with benzene and forming toluene in situ prior to converting such toluene to C8 aromatics. The mixture of C8 aromatics produced in step (ii) may comprise from 75 to 98 volume percent, for example, from 80 to 95 volume percent of paraxylene.

The mixtures of C8 aromatics from steps (i) and (ii) are, at least in part, introduced to a simulated moving-bed adsorption apparatus.

According to a third step, i.e. step (iii), of the overall process for making paraxylene, at least a portion of the mixture of C8 aromatics from step (i) is passed through a rotary valve and then through a conduit and then into a bed of a simulated countercurrent adsorptive separation unit. The simulated countercurrent adsorptive separation unit comprises a series of beds of adsorbent. The beds are each included in adsorbent bed chambers. Beds are stacked one on top of another throughout at least one column, wherein liquid flows continuously in a downward manner from the top of one bed, through the bed, and then to the top of the next bed in the series. Within an individual column, beds are stacked one on top of the other. When the beds are contained in more than one column, circulating fluid from the bottom of one column flows through a conduit and then into the top of the next column connecting the beds in series. The effluent from the bottom of the last column in the series is passed through a conduit to the top of the first column in the series. The affinity of the adsorbent in the beds to adsorb paraxylene is greater the affinity of the adsorbent to adsorb any of metaxylene, orthoxylene, and ethylbenzene. The mixture of C8 aromatics, which is introduced as a feed according to step (iii), comprises from 15 to 30 volume percent of paraxylene.

Whereas the product from a non-selective process, such as reforming, transalkylation, and isomerization, is used as a feed in step (iii), in step (iv) the product of a selective process, such as a selective toluene disproportionation process and/or a selective alkylation process, is used as a portion of a flushing medium to displace residual feed in a conduit of a bed, which is located upstream, in terms of the direction of flow of circulating fluid, from the bed of step (iii) in which feed is introduced.

Step (iv) of an embodiment of a process of the present invention may be characterized as a first or primary flushing step. In step (iv), at least a portion of the mixture of C8 aromatics from step (ii) is passed through a rotary valve and then through a conduit in fluid communication with the rotary valve and a bed of the simulated countercurrent adsorptive separation unit. The bed of step (iii) is different than the bed of step (iv). The bed of step (iii) is located downstream, based on the direction of the flow of circulating bulk fluid, from the bed of step (iv). The volume of the mixture of C8 aromatics from step (ii) introduced into the conduit in step (iv) may be less than the total volume of the conduit.

After the primary flushing step (iv) takes place, residual primary flushing remains in the conduit. This primary flushing medium displaced from a conduit, which had previously been used in a primary flushing step, by a second or secondary flushing step. Such a secondary flushing step, according to embodiments described herein, is labeled herein as step (v). In step (v), a liquid is passed through a rotary valve and then through a conduit in fluid communication with the rotary valve and a bed chamber of the simulated moving-bed adsorptive separation unit. The bed of step (iii) and the bed of step (iv) are both different than the bed of step (v). The bed of step (iv) is located downstream, based on the direction of the flow of circulating bulk fluid, from the bed of step (v). The liquid passed into the conduit of step (v) comprises less than 1 volume percent of ethylbenzene, less than 2 volume percent of orthoxylene and less than 2 volume percent of metaxylene. The secondary flushing step (v), if necessary, reduces the amount of residual ethylbenzene, metaxylene, and orthoxylene in the conduit to acceptable levels, so that an extract stream may be withdrawn through the conduit without undue contamination of the extract with the residual ethylbenzene, metaxylene, and orthoxylene.

An extract stream is withdrawn from a conduit, which had previously been flushed with a primary flushing step and, if used, a secondary flushing step. According to embodiments described herein, an extraction step is labeled herein as step (vi). In step (vi), an extract stream comprising a desorbent and paraxylene from a bed of the simulated countercurrent adsorptive separation unit is withdrawn through a conduit and then through a rotary valve. The bed of step (iii), the bed of step (iv) and the bed of step (v) are all different than the bed of step (vi). The bed of the primary flushing step (iv) and the bed of the secondary flushing step (v) are located downstream, based on the direction of the flow of circulating bulk fluid, from the bed of step (vi).

A desorbent stream is introduced into a conduit, which had been previously been used to withdraw an extract stream. According to embodiments described herein, this desorbent stream is introduced in a step labeled herein as step (vii). In step (vii), desorbent is passed through a rotary valve and then through a conduit and then into a bed of the simulated countercurrent adsorptive separation unit. The bed of step (iii), the bed of step (iv), the bed of step (v) and the bed of step (vi) are all different than the bed of step (vii). The bed of step (vi) is located downstream, based on the direction of the flow of circulating bulk fluid, from the bed of step (vii).

As described above, at least a portion of the mixture of C8 aromatics of step (i) may be formed by a reforming process. The reforming process may comprise passing a mixture of hydrocarbons comprising naphtha into a reforming unit. In the reforming unit, at least a portion of the naphtha in the reforming unit is converted into aromatic compounds comprising benzene, toluene, xylenes and ethylbenzene. The effluent from the reforming unit may be distilled to separate xylenes and ethylbenzene from other aromatics. The naphtha feed comprises a mixture of hydrocarbons comprising C6, C7, and C8 paraffins.

As also described above, at least a portion of the mixture of C8 aromatics used as a feed in step (i) may be formed by a transalkylation process. The transalkylation process may comprise passing a mixture of toluene and trimethylbenzene into a transalkylation unit. At least a portion of the toluene and trimethylbenzene in the transalkylation unit is converted into aromatic compounds comprising xylenes and ethylbenzene.

As further described above, at least a portion of the mixture of C8 aromatics used as a feed in step (i) may be formed by an isomerization process. Xylenes obtained from a raffinate stream may be used as a feed to this isomerization process.

A raffinate stream may be withdrawn from a simulated moving bed adsorption apparatus in a step labeled herein as step (viii). In step (viii), a raffinate stream comprising a desorbent, metaxylene, orthoxylene, and ethylbenzene is withdrawn from a bed of the simulated countercurrent adsorptive separation unit through a conduit and then through a rotary valve. The bed of step (iii), the bed of step (iv), the bed of step (v), the bed of step (vi), and the bed of step (vii) are all different than the bed of step (viii). The bed of step (vii) is downstream, based on the direction of the flow of circulating bulk fluid, from the bed of step (iii). The raffinate stream comprises desorbent, metaxylene, orthoxylene, and ethylbenzene.

The raffinate stream from step (viii) may be distilled in a step labeled herein as step (ix). In step (ix), the raffinate stream from step (viii) is distilled to obtain a stream enriched in desorbent and a stream enriched in C8 aromatics comprising metaxylene, orthoxylene, and ethylbenzene.

The C8 aromatics from step (ix) may be isomerized in a step labeled herein as step (x). In particular, in step (x) the stream enriched in C8 aromatics from step (ix) is passed to an isomerization unit to obtain an isomerized product stream comprising from 15 to 30 volume percent, for example, from 20 to 30 volume percent of paraxylene.

The isomerized product stream may then be fed to the overall adsorption process in a step labeled herein as step (xi). In step (xi), at least a portion of isomerized product stream from step (x) is passed to the adsorbent bed of step (iii).

The simulated movement or countercurrent flow of adsorbent beds is achieved by redirecting the flow of liquids, other than the circulating bulk fluid, to and from beds of the adsorption chamber. This redirection may be achieved, while the continuous flow of circulating bulk fluid is maintained. In one embodiment, the flow of streams, which comprise feed, flushing fluids, extract, desorbent and raffinate, to and from the beds of steps iii-viii is discontinued, and then the flow of these streams is resumed in the next beds in the series of beds downstream, in terms of the direction of flow on the circulating bulk fluid. For example, over time, the flow of liquids, other than the circulating bulk fluid, into and out of the beds of the steps (iii), (iv), (v), (vi), (vii), and (viii) is discontinued and the flow of liquids into and out of the beds is resumed in the beds immediately downstream of the beds, in terms of the direction of the flow of circulating bulk fluid.

EXAMPLES

In the Examples, which follow, paraxylene is separated from other C8 aromatics in a Parex™ unit. The unit comprises two columns in fluid communication with a rotary device. Each column comprises twelve adsorbent bed chambers, stacked one on top of the other, containing a molecular sieve adsorbent. For the purposes of explanation, these beds are identified as beds 1 to 24. The number of beds described in each zone are for illustrative purposes and the number of beds may be varied without changing the concepts described herein.

In the first column, the beds are stacked, such that fluid, which is introduced into the top of a first column, flows downward through the top of the column to the bed (i.e. bed 1) at the top of the stack of beds and then through beds below to the bed (i.e. bed 12) at the at the bottom of the column. Fluid from the bottom end of the first column then flows to the top of a second column. Fluid, which is introduced into the top of the second column, flows downward through the column to the bed (i.e. bed 13) at the top of the stack of beds to the bed (i.e. bed 24) at the bottom of the column. Fluid from the bottom end of the second column then flows to the top of a first column to complete a circulation loop of circulating bulk fluid throughout the columns.

When feed is first introduced into the adsorption apparatus, this initial introduction of feed may take place in any of the beds of the apparatus. For example, feed may be introduced to the top of the first column. The feed is primarily composed of C8 aromatics having 23 percent paraxylene and 77 percent of a mixture of metaxylene, orthoxylene, and ethylbenzene. The feed also includes small amounts of impurities including toluene and paraffins. The feed is a mixture of product streams from a reforming process, a transalkylation process and an isomerization process.

Feed, which is introduced into the top of the first column, becomes adsorbed in the adsorbent in the first catalyst bed. The adsorbent in the adsorption apparatus is a molecular sieve adsorbent. Feed continues to be introduced into the first adsorbent bed until at least a portion of the feed is carried downward with the flow of circulating bulk fluid to the second catalyst bed (i.e. bed 2) and even as far as the third adsorbent bed (i.e. bed 3).

As feed stream is being fed into bed 1, a liquid withdrawal stream is taken from bed 7, a desorbent stream is introduced into bed 10, and another withdrawal stream is taken from bed 15. The desorbent introduced into the adsorption apparatus is paradiethylbenzene.

After a predetermined period of time, a rotary valve device shifts the flow of these streams. In each shift, the flow of these streams is redirected to a bed immediately downstream, in terms of the direction of circulating fluid through the columns. In particular, in a first shift, the flow of feed stream is redirected from bed 1 to bed 2, the flow of liquid withdrawal stream from bed 7 is redirected to bed 8, the flow of desorbent into bed 10 is redirected to bed 11, and the flow of liquid withdrawn from bed 15 is redirected to bed 16. Each shift of the direction of stream flow is also referred to as a valve step.

In the initial stages of feed introduction, e.g., during the start-up stage of the unit, there is an insufficient amount of C8 aromatics to advance downstream to the point where liquid is first withdrawn from the circulating bulk fluid. Also, in these initial stages, there have been an insufficient number of valve steps to push beds with C8 aromatics upstream to the point between the introduction of the desorbent and the introduction of feed, where a second withdrawal stream is taken. However, as the rotary valve device controlling these streams advances through a sufficient number of valve steps, the number of beds comprising C8 aromatics downstream and upstream from the bed to which feed is introduced increases.

Eventually, liquid C8 aromatics will be present in each of the beds downstream of the bed to which feed is introduced and the bed where a first withdrawal stream is taken. The circulating bulk fluid will become increasingly depleted in paraxylene in beds located furthest downstream from the bed to which feed is introduced. Eventually, the liquid withdrawn from the bed located 6 beds downstream from the bed to which feed is introduced, will have a concentration of paraxylene, based on the total of C8 aromatics, of less than about 1-2 percent, typically paraxylene recoveries are greater than 95%. At this point in time, the stream withdrawn from the bed, which is six beds downstream from the bed to which feed is introduced, may be characterized as a raffinate stream.

After sufficient number of valve steps of the process has taken place, liquid C8 aromatics will be present in each of the beds upstream of the bed to which feed is introduced and the bed where a second withdrawal stream is taken. The circulating bulk fluid will become increasingly enriched in paraxylene in beds located furthest upstream from the bed to which feed is introduced. Eventually, the liquid withdrawn from the bed located 10 beds upstream from the bed to which feed is introduced, will have a concentration of paraxylene, based on the total of C8 aromatics, of greater than about 99 percent. At this point in time, the stream withdrawn from the bed, which is ten beds upstream from the bed to which feed is introduced, may be characterized as an extract stream.

When a sufficient number of valve steps of the process have taken place to establish raffinate and extract streams, the beds of the apparatus may be described in terms of four zones, i.e. a desorption zone, a purification or rectification zone, an adsorption zone and a buffer zone. The desorption zone includes the bed to which a desorbent stream is introduced and the four beds downstream from this bed terminating in the bed from which the extract stream is withdrawn. The purification zone includes the nine beds immediately downstream of desorption zone, terminating in with the bed immediately upstream from the bed to which feed is introduced. The adsorption zone includes the bed to which feed is introduced and the six beds immediately downstream of the purification zone terminating in the bed from which a raffinate stream is withdrawn. The buffer zone includes the six beds immediately downstream from the purification zone and terminating in the bed immediately upstream from the desorption zone.

The reformate and extract streams pass through conduits and through the rotary valve device. These streams are then distilled to separate paradiethylbenzene from C8 aromatics. A paraxylene product is recovered from the distillation of the extract stream. Paradiethylbenzene is recycled to the adsorption process as desorbent. C8 aromatics obtained by distillation of the raffinate stream are passed to an isomerization unit to convert a portion of these C8 aromatics to paraxylene. The isomerized C8 aromatics are then used as a portion of the feed to the adsorption process. Paradiethylbenzene recovered by distillation of the raffinate stream is also recycled to the adsorption process as desorbent.

The adsorption zone is provided with two flush streams. In particular, a first or primary flush stream passes through the rotary valve device and trough a conduit to displace residual feed in the conduit into a bed, which is two beds upstream, in terms of the direction of flow of circulating fluid, from the bed to which feed is introduced. For example, when feed is introduced to bed 1, the primary flushing fluid will be introduced into bed 23. The primary flush stream will be shifted one bed downstream, in terms of the direction of the flow of the circulating fluid, along with other inlet and withdraw streams with each valve step of the process.

A second or secondary flush stream also passes through the rotary valve device and through a conduit to displace residual primary flush fluid in the conduit into a bed, which is nine beds upstream, in terms of the direction of flow of circulating fluid, from the bed to which feed is introduced.

The bed to which the secondary flush stream is directed is also one bed downstream, in terms of the direction of the flow of circulating bulk fluid, from the bed from which an extract stream is withdrawn. For example, when feed is introduced to bed 1, the primary flush fluid will be directed to bed 23, the secondary flush fluid will be directed to bed 16, and the extract stream will be taken from bed 15.

A liquid withdrawal stream is also taken from the desorption zone. In particular, the liquid withdrawal stream is taken from the bed located one bed downstream from the bed to which the desorbent stream is introduced. For example, when feed is introduced to bed 1, the primary flush fluid will be directed to bed 23, the secondary flush fluid will be directed to bed 16, the extract stream will be taken from bed 15, the liquid withdrawal stream will be taken from bed 11, and the desorbent stream (i.e. a paradiethylbenzene stream) will be introduced to bed 10.

In the Examples, which follow, a C8 aromatic feed stream is introduced into the bed 1 of the 24-bed simulated moving bed adsorption apparatus described above. The C8 aromatic feed has 23 percent paraxylene and 77 percent of a mixture of metaxylene, orthoxylene, and ethylbenzene. This feed is introduced the bed during a first valve step of the adsorption process.

After two process valve steps, a third valve step is started. At the start of the third valve step, bed 1 has now been shifted to a location two beds above the bed (i.e. bed 3) where feed is now being introduced. At the start of the third valve step, the conduit leading to bed 1 is filled with residual feed. The volume of this conduit is 0.68 m$^3$.

During the third valve step, a primary flushing medium is introduced through a rotary valve device and into the conduit, which is in fluid communication with bed 1.

After the process advances eight more valve steps, a ninth valve step takes place. At the start of the ninth valve step, the conduit connected to bed 1 is filled with a residue of the primary flushing medium and, perhaps, a small residue (e.g., a trace) of C8 aromatics from the feed. During the ninth valve step, a secondary flushing medium is introduced through a rotary valve device and into the conduit, which is in fluid communication with bed 1.

After the process advances one more valve step, a tenth valve step takes place. At the start of the tenth valve step, the conduit connected to bed 1 contains a residue of the secondary flushing medium introduced in valve step 9 and, perhaps, a small amount of C8 aromatics introduced into the conduit during valve steps 1 and 3. During the tenth valve step an extract stream, which comprises paradiethylbenzene and paraxylene, is withdrawn from the conduit connected to bed 1 and through the rotary valve device.

After the process advances four more valve steps, a fourteenth valve step takes place. During the fourteenth valve step, a liquid withdraw stream is withdrawn through the conduit connected to bed 1. After the process advances one more valve step, a fifteenth valve step takes place. During the fifteenth valve step, a paradiethylbenzene desorbent stream is introduced into bed 1.

Example 1

Comparative

In this Example, the primary flush step conducted during valve step 3 is conducted with a desorbent stream. The secondary flush step conducted during valve step 9 is also conducted with a desorbent stream. The desorbent may comprise recycled paradiethylbenzene obtained from distillation of the extract or raffinate obtained from the process. The desorbent may also comprise at least a portion of a liquid withdrawal stream obtained from a bed located one bed downstream from the bed at the end of the desorption zone where paradiethylbenzene is introduced to cause desorption of C8 aromatics from the adsorbent.

The volume of paradiethylbenzene introduced during the primary flushing step to the conduit connected to bed 1 is 1.02 m$^3$, which is 150% of the volume of the conduit, and the volume of the paradiethylbenzene introduced during the secondary flushing step to the conduit connected to bed 1 is 0.68 m$^3$, which is 100% of the volume of the conduit. The primary flushing step displaces essentially all of the residual feed material from the conduit and into bed 1. Since the conduit volume is 0.68 m$^3$, and the residual feed has 77 percent of a mixture of metaxylene, orthoxylene, and ethylbenzene, the primary flushing step results in 0.52 m$^3$ (77% of 0.68=0.52) of a mixture of metaxylene, orthoxylene, and ethylbenzene being introduced into bed 1. However, since bed 1 is located during valve step 3 sufficiently downstream, in terms of the flow of circulating bulk fluid, from the point where an extract stream is withdrawn, the non-paraxylene C8 aromatics introduced during the primary flushing step will separate from paraxylene before an extract is withdrawn from the process. Essentially no C8 aromatics are introduced into bed 1 during the secondary flushing step. The process of this Example gives good results in terms of flushing metaxylene, orthoxylene, and ethylbenzene from the conduit and limited introduction of these C8 aromatics into bed 1, particularly during the secondary flushing step. However, this process also results in considerable amounts of desorbent being introduced into bed 1 in the purification zone. In particular, since 1.02 m$^3$ of paradiethylbenzene is introduced into the conduit, and since the conduit volume is only 0.68 m$^3$, 0.34 m$^3$ (1.02 m$^3$ minus 0.68 m$^3$) of paradiethylbenzene is introduced into the adsorbent bed during the primary flushing step.

Introduction of desorbent at this stage causes competition for the adsorbent selective sites and may cause excess desorption of paraxylene before the bed progresses through the purification zone. This introduction of desorbent, in the end, results in reduced efficiency and lower ultimate capacity of the adsorbent system. This reduction in capacity could be in the range of from 3-10% depending on the exact operations. The use of this amount (1.02 m$^3$) of desorbent in the primary flush step also increases utility consumption in order to fractionate and circulate higher desorbent rates. It would be desirable to use less desorbent in the purification zone and more desorbent in the desorption zone.

Example 2

Comparative

In this Example, the primary flush step, which is conducted during valve step 3, is conducted with a stream of enhanced paraxylene from a selective toluene disproportionation process. The enhanced paraxylene stream comprises 90 percent paraxylene and 10 percent of a mixture of metaxylene, orthoxylene, and ethylbenzene. The secondary flush step, which is conducted during valve step 9, is also conducted with this enhanced paraxylene stream.

The volume of the enhanced paraxylene stream introduced during the primary flush step to the conduit connected to bed 1 is 1.02 m$^3$, which is 150% of the volume of the conduit, and the volume of the enhanced paraxylene stream introduced during the secondary flush step to the conduit connected to bed 1 is 0.68 m$^3$, which is 100% of the volume of the conduit. The primary flush step displaces essentially all of the residual feed material from the conduit and into bed 1. Since the conduit volume is 0.68 m$^3$, and the residual feed has 77 percent of a mixture of metaxylene, orthoxylene, and ethylbenzene, the primary flush step results in at least 0.52 m$^3$ (77% of 0.68=0.52) of a mixture of metaxylene, orthoxylene, and ethylbenzene to be introduced into bed 1. However, additional metaxylene, orthoxylene, and ethylbenzene is also introduced into bed 1 from the enhanced paraxylene stream. Since the volume of enhanced paraxylene stream exceeds the volume of the conduit by 0.34 m$^3$ and the enhanced paraxylene stream has 10 percent of a mixture of metaxylene, orthoxylene, and ethylbenzene, an additional 0.03 m$^3$ (10 percent of 0.34 is approximately 0.03) of metaxylene, orthoxylene, and ethylbenzene is also introduced into bed 1 from the enhanced paraxylene stream. Accordingly, 0.56 m$^3$ of a mixture of metaxylene, orthoxylene, and ethylbenzene, is introduced into bed 1 during the primary flushing step conducted during valve step 3.

Although the amount of the mixture of metaxylene, orthoxylene, and ethylbenzene introduced into bed 1 (0.56 m$^3$) during the primary flush step of Example 2 is greater than the amount of the mixture of metaxylene, orthoxylene, and ethylbenzene introduced into bed 1 (0.52 m$^3$) during the primary flushing step of Example 1, bed 1 is still located during valve step 3 sufficiently downstream, in terms of the flow of circulating bulk fluid, from the point where an extract stream is withdrawn, such that the non-paraxylene C8 aromatics introduced during the primary flush step will separate from paraxylene before an extract is withdrawn from the process. However, a considerable amount of these C8 aromatic isomers will remain in the conduit and will be flushed out the conduit into bed during the secondary flush step of valve step 9.

In the secondary flush step, conducted six valve steps after the primary flush step, the residue of the enhanced paraxylene in the conduit is flushed into bed 1. Since this residue comprises 10 percent of a mixture of metaxylene, orthoxylene, and ethylbenzene, and the volume of the C8 aromatics flushed into bed 1 is 0.68 m$^3$, approximately 0.07 m$^3$ (10% of 0.68 is approximately 0.07) of metaxylene, orthoxylene, and ethylbenzene are introduced into bed 1 during the secondary flush step.

The introduction of 0.07 m$^3$ of non-C8 paraxylene aromatics (e.g., metaxylene, orthoxylene, and ethylbenzene) into bed 1 according to Example 2 is problematic. In the next valve step (i.e. valve step 10), an extract stream is taken from bed 1. There are not enough valve steps and beds intervening between the extraction step and the secondary flush step to satisfactorily separate paraxylene from other C8 aromatics (i.e. metaxylene, orthoxylene, and ethylbenzene) to provide an extract stream sufficiently free of metaxylene, orthoxylene, and ethylbenzene.

In order to better separate paraxylene from other C8 aromatics, the secondary flush stream of Example 2 should be introduced to a bed further downstream, in terms of the flow of circulating bulk fluid. In particular, the secondary flush stream could be redirected to a bed four beds downstream, in terms of the direction of the flow of circulating bulk fluid, from the bed from which the extract stream is withdrawn. With this redirection, a sufficient number of intervening valve steps and beds are introduced to allow proper separation of paraxylene from other C8 aromatics to occur before an extract stream is taken from bed 1. However, in order to accomplish this redirection, the rotary valve device may need to be reconfigured, resulting in an expensive modification of the rotary valve device.

Additionally, the residue of the enhanced paraxylene stream remaining in the conduit to bed 1 at the termination of the secondary flushing step includes 0.07 m$^3$ of non-C8 paraxylene aromatics (e.g., metaxylene, orthoxylene, and ethylbenzene). When an extract stream is taken from bed 1 in valve step 10, these unwanted aromatics will be carried into the extract stream.

Accordingly, the process of this comparative Example 2, results in a considerable amount of contaminants (e.g., metaxylene, orthoxylene, and ethylbenzene) being introduced into the last stages of the adsorption unit purification zone, thereby requiring adjustments in the purification zone and adsorption zone operations which decrease unit capacity and increase utilities.

Example 3

Inventive

In this Example, the primary flush step, which is conducted during valve step 3, is conducted with a mixture of a stream of enhanced paraxylene from a selective toluene disproportionation process and a stream of desorbent (i.e. paradiethylbenzene). The enhanced paraxylene stream comprises 90 percent paraxylene and 10 percent of a mixture of metaxylene, orthoxylene, and ethylbenzene. The secondary flush step, which is conducted during valve step 9, involves the use of paradiethylbenzene as a secondary flushing medium.

In the primary flush step, enhanced paraxylene and desorbent are introduced sequentially. In particular, 0.51 m$^3$ (i.e. 75 percent of the conduit volume) of enhanced paraxylene is first introduced through the rotary valve device into the conduit. Then, 0.51 m$^3$ (i.e. 75 percent of the conduit volume) of paradiethylbenzene is introduced into the conduit. This primary flush step displaces all of the feed residue and a portion of the enhanced paraxylene into bed 1. Since the conduit volume is 0.68 m$^3$, and the residual feed has 77 percent of a mixture of metaxylene, orthoxylene, and ethylbenzene, the displacement of the residual feed results in 0.52 m$^3$ (77% of 0.68=0.52) of a mixture of metaxylene, orthoxylene, and ethylbenzene being introduced into bed 1. The displacement of enhanced paraxylene, which comprises 10 percent of a mixture of metaxylene, orthoxylene, and ethylbenzene, results in the added introduction of approximately 0.02 m$^3$ of a mixture of metaxylene, orthoxylene, and ethylbenzene into bed 1. Therefore, a total of 0.54 m$^3$ of a mixture of metaxylene, orthoxylene, and ethylbenzene, is introduced into bed 1 during the primary flush step. Since desorbent (i.e. paradiethylbenzene) is introduced after the enhanced paraxylene, the desorbent does not reach bed 1. It is desirable to avoid introducing desorbent into bed 1 during the primary flush step.

The amount of a mixture of metaxylene, orthoxylene, and ethylbenzene, which is introduced into bed 1 during the primary flush step, is not significantly different than the amount of this mixture introduced during the primary flush step of Example 1. None of this mixture would remain in bed 1 when the process has advanced to the stage of valve step 10, when an extract stream is withdrawn from bed 1. Therefore, the primary flush step would not contribute to contamination of the extract stream with a mixture of metaxylene, orthoxylene, and ethylbenzene.

The displacement of enhanced paraxylene into bed 1 during the primary flush step does, however, provide an advantage in that extra paraxylene is introduced into bed 1. This extra paraxylene increases the yield of paraxylene taken from the extract stream. Another advantage of the process of Example 3, in comparison with the process of Example 1, is that essentially no desorbent is introduced into bed 1 during the primary flush step (valve step 3).

After the primary flush step, a small amount of a mixture of metaxylene, orthoxylene, and ethylbenzene remains in the conduit as part of the residue of the enhanced paraxylene remaining in the conduit. In the secondary flush step, the conduit is flushed with 0.68 m$^3$ (100% of the conduit volume) of paradiethylbenzene. The secondary flush step, thus, displaces all of the residual mixture (i.e. about 0.02 m$^3$) into bed 1. However, this amount (0.02 m$^3$) is much smaller than the amount (0.07 m$^3$) of a mixture of metaxylene, orthoxylene, and ethylbenzene introduced into bed 1 during the secondary flush step of Example 2. This smaller amount can be tolerated in valve step 9, such that the rotary valve device would not need to be reconfigured to cause the secondary flush step to take place in an earlier valve step. Furthermore, in comparison with the process of Example 1, essentially no desorbent from the secondary flushing medium is introduced into bed 1 during the secondary flush step. Moreover, in comparison with the process of Example 2, essentially no metaxylene, orthoxylene, and ethylbenzene remains in the conduit after valve step 9 to be withdrawn with the extract stream in valve step 10.

Example 4

Inventive

Example 3 is repeated, except that enhanced paraxylene and paradiethylbenzene are not added in sequence. In Example 4, enhanced paraxylene and paradiethylbenzene are mixed together before passing through the rotary valve device and into the conduit to bed 1 during the primary flush step. The process of Example 4 results in acceptable levels of metaxylene, orthoxylene, and ethylbenzene in the extract stream.

Example 5

Inventive

Example 3 is repeated except that the amount of enhanced paraxylene and paradiethylbenzene in the primary flush step is increased. In particular, during valve step 3, 0.68 m$^3$ (100% of the conduit volume) of enhanced paraxylene is first introduced into the conduit followed by 0.68 m$^3$ (100% of the conduit volume) of paradiethylbenzene. As a result of displacement of liquid in the conduit, 0.59 m$^3$ of a mixture of metaxylene, orthoxylene, and ethylbenzene is introduced into bed 1 during the primary flushing step. Also, essentially all of the metaxylene, orthoxylene, and ethylbenzene is removed from the conduit during the primary flush step. The metaxylene, orthoxylene, and ethylbenzene introduced into bed 1 during valve step 3 are separated from paraxylene prior to the extraction step during valve step 9.

Since essentially all of the metaxylene, orthoxylene, and ethylbenzene is removed from the conduit during the first of primary flush step, this Example 5 may be conducted with or without a second or secondary flush step.

Example 6

Inventive

A refinery includes a reformer and a Parex™ Unit. The reformer produces 1250 KTA (Kilo Tons per Annum) refor-mate yielding approximately 400 KTA xylenes and 250 KTA toluene. This toluene is fed to a selective toluene disproportionation unit. A yield of 50% enhanced paraxylene is achieved, which provides 125 KTA (~15 tons/hr) of xylenes comprising about 90% paraxylene. The Parex™ Unit line flush requirement would be ~40 m$^3$/hr at flowing conditions (translating to ~30 tons/hr) requirement. Therefore, the amount of xylenes from the selective toluene disproportionation unit is only about half of what is needed to flush the conduits of the conduit volume of the Parex™ Unit, even in a single primary flush.

In a primary flush step, enhanced paraxylene from the selective toluene disproportionation unit is first introduced into the conduit in an amount sufficient to displace about 50 volume percent of the fluid in the conduit. Then, the primary flush step is completed by introducing a sufficient amount of paradiethylbenzene into to the conduit to displace the enhanced paraxylene introduced into the conduit. In particular, the volume of paradiethylbenzene introduced into the conduit is 100% of the conduit volume.

This Example 6 may be conducted with or without a second or secondary flush step.

The invention has been described above with reference to numerous embodiments and specific examples. Many variations will suggest themselves to those skilled in this art in light of the above detailed description. All such obvious variations are within the full intended scope of the appended claims.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process for separating paraxylene from at least one multicomponent feed by simulated countercurrent adsorptive separation in an apparatus comprising at least one column comprising multiple adsorbent bed chambers comprising adsorbent beds stacked one on too of the other, wherein a circulating bulk fluid flows into the top of an adsorbent bed chamber, through the adsorbent bed and down to the top of the next adsorbent bed chamber, said process comprising the steps of:

(a) passing said multicomponent feed through a conduit into an absorbent bed in an adsorbent bed chamber to adsorb paraxylene on said adsorbent, wherein the multicomponent feed comprises a C8 aromatic mixture of paraxylene, orthoxylene, metaxylene, and ethylbenzene, said C8 aromatic mixture comprising from 15 to 30 volume percent of paraxylene, (b) passing at least one first flushing medium into conduit of step (a) in fluid communication with the adsorbent bed chamber to flush residue of the multicomponent feed from the conduit and into the adsorbent bed of the adsorbent bed chamber comprising adsorbed paraxylene, wherein the first flushing medium comprises from 10 to 95 volume percent, based on the total volume of the first flushing medium, of a C8 aromatic mixture and from 5 to 70 volume percent of a non-C8 aromatic liquid, which is miscible with C8 aromatics, and wherein the C8 aromatic mixture in the first flushing medium comprises from 75 to 98 volume percent of paraxylene;

(c) passing at least one second flushing medium into the conduit of step (b) in fluid communication with the adsorbent bed chamber to flush residue of the first flushing medium from the conduit into the adsorbent bed of the adsorbent bed chamber, wherein the second flushing medium comprises less than 1 volume percent of ethylbenzene, less than 2 volume percent of orthoxylene, and less than 2 volume percent of metaxylene; and (d) withdrawing an extract stream comprising paraxylene from the conduit of step (c) after the second adsorbent bed has been subjected to said second flushing step (c).

2. The process of claim 1, wherein the sum of orthoxylene, metaxylene, and ethylbenzene make up 70 to 85 volume percent of the multicomponent feed of step (a), and wherein the volume of the C8 aromatic mixture introduced into the conduit during step (b) is from 10 to 100 percent of the volume of the conduit.

3. The process of claim 1, wherein the volume of the C8 aromatic mixture introduced into the conduit during step (b) is from 30 to 95 percent of the volume of the conduit.

4. The process of claim 1, wherein the first flushing step of step (b) comprises introducing the C8 aromatics and the non-C8 aromatics into the conduit together.

5. The process of claim 1, wherein the first flushing step of step (b) comprises sequentially passing into the conduit the C8 aromatic mixture, followed by passing the non-C8 aromatic liquid into the conduit.

6. The process of claim 1, wherein the non-C8 aromatic liquid and the second flushing medium comprises at least one hydrocarbon selected from the group consisting of paradiethylbenzene, toluene, tetralin, cyclohexane, and paraffins having from 6 to 20 carbon atoms.

7. The process of claim 1, wherein said apparatus further comprises at least one rotary valve, wherein the conduit of steps (a), (b), and (c) provides fluid communication between the adsorbent bed chamber and the at least one rotary valve, and wherein the at least one rotary valve controls the direction of fluid flow through the conduit of steps (a), (b), and (c).

8. The process of claim 7, further comprising the step of:
(e) passing a desorbent through a rotary valve and the conduit to the adsorbent bed chamber after the extract stream has been withdrawn from the adsorbent bed chamber according to step (d).

9. The process of claim 8, further comprising the step of:
(f) withdrawing a portion of the liquid from the adsorbent bed chamber through the conduit and a rotary valve before desorbent has been passed through the conduit into the adsorbent bed chamber according to step (e) and after a liquid stream has been removed from said chamber through the conduit according to step (d).

10. The process of claim 1, wherein said second flushing medium of step (c) comprises less than 1.0 volume percent of the sum of paraxylene, orthoxylene, metaxylene, and ethylbenzene, and wherein the second flushing medium comprises at least 99 volume percent of the desorbent used in step (e).

11. The process of claim 9, wherein at least of a portion of the liquid withdrawn according to step (f) is used as the second flushing fluid of step (c).

12. The process of claim 7,
wherein separate conduits provide fluid communication between each adsorbent bed chamber and the at least one rotary valve.

13. The process of claim 12, wherein the flow of liquids through conduits to and from adsorbent bed chambers are controlled by the at least one rotary valve, such that, over time, each of steps (a), (b), (c), (d), (e), and (f) take place in each of the adsorbent bed chambers of the apparatus.

14. The process of claim 13, wherein, at the same time that the multicomponent feed is passed through a rotary valve through a first conduit into a first adsorbent bed in a first adsorbent bed chamber according to step (a), the following steps occur:

(b') the at least one first flushing medium is passed through a rotary valve and then into a second conduit in fluid communication with a second adsorbent bed chamber to flush residue of the multicomponent feed from the second conduit and into the adsorbent bed of the second adsorbent bed chamber, wherein the second adsorbent bed chamber is located upstream from the first adsorbent bed chamber, based on the direction of the flow of the circulating bulk fluid;

(c') the at least one second flushing medium s passed through a rotary valve and then into a third conduit in fluid communication with a third adsorbent bed chamber to flush residue of the first flushing medium the third conduit into the adsorbent bed of the third adsorbent bed chamber, wherein the third adsorbent bed chamber is located upstream from the second adsorbent bed chamber, based on the direction of the flow of the circulating bulk fluid;

(d') an extract stream is passed through a fourth conduit and then into a rotary valve, wherein the fourth conduit is in fluid communication with a fourth adsorbent bed chamber, wherein the fourth adsorbent bed chamber is located upstream from the third adsorbent bed chamber, based on the direction of the flow of the circulating bulk fluid; and (e') the desorbent is passed through a rotary valve and then into a fifth conduit in to fluid communication with a fifth adsorbent bed chamber located above said fourth adsorbent bed chamber, wherein the fifth adsorbent bed chamber is located upstream from the fourth adsorbent bed chamber, based on the direction of the flow of the circulating bulk fluid.

15. The process of claim 14, further comprising the step of:

(f) withdrawing a liquid from a sixth adsorbent bed chamber into a sixth conduit and then through a rotary valve, wherein the sixth adsorbent bed chamber is located upstream from the fourth adsorbent bed chamber and downstream from the fifth adsorbent bed chamber, based on the direction of the flow of circulating bulk fluid, and wherein at least a portion of the liquid withdrawn according to step (f) is used as at least a portion of the at least one second flushing medium.

16. The process of claim 15, wherein at least one adsorbent bed chamber is located upstream, based on the direction of the flow of circulating bulk fluid, from the adsorbent bed chamber into which the first flushing medium is introduced according to step (b') and downstream, based on the direction of the flow of circulating bulk fluid, from the adsorbent bed chamber into which the secondary flushing medium is introduced according to step (c'), and wherein at least one adsorbent bed chamber is located upstream, based on the direction of the flow of circulating bulk fluid, from the adsorbent bed chamber from which 30 extract fluid is withdrawn according to step (d') and downstream, based on the direction of the flow of circulating bulk fluid, from the adsorbent bed chamber from which liquid is withdrawn according to step (f).

17. The process of claim 8, wherein the extract stream withdrawn according to step (d) or (d') comprises at least 99.7 volume percent of paraxylene, based on the total volume of xylenes and ethylbenzene present in said extract stream.

18. A process for separating paraxylene from at least one multicomponent feed by simulated countercurrent adsorptive separation in an apparatus comprising at least one column comprising multiple adsorbent bed chambers comprising adsorbent beds stacked one on top of the other, wherein a circulating bulk fluid flows into the top of an adsorbent bed chamber, through the adsorbent bed and down to the top of the next adsorbent bed chamber, said process comprising the steps of:
  (a) passing said multicomponent feed through a first conduit into a first absorbent bed in a first adsorbent bed chamber to adsorb paraxylene on said adsorbent, wherein the multicomponent feed comprises at least 50 volume percent of a C8 aromatic mixture of paraxylene, orthoxylene, metaxylene, and ethylbenzene, said C8 aromatic mixture being produced by at least one refinery or petrochemical process, and said C8 aromatic mixture comprising from 15 to 30 volume percent of paraxylene,
  (b) passing at least one first flushing medium into a second conduit in fluid communication with a second adsorbent bed chamber to flush residue of the multicomponent feed from the second conduit and into the adsorbent bed of the second adsorbent bed chamber comprising adsorbed paraxylene, wherein the second adsorbent bed chamber is located upstream from the first adsorbent bed chamber, based on the direction of the flow of the circulating bulk fluid,
  wherein the first flushing medium comprising from 5 to 90 volume percent of a non-C8 aromatic, and further comprises from 10 to 95 volume percent of a C8 aromatic mixture of paraxylene, orthoxylene, metaxylene, and ethylbenzene, said C8 aromatic mixture being produced by at least one refinery or petrochemical process, and said C8 aromatic mixture comprising from 75 to 98 volume percent of paraxylene,
  (c) passing at least one second flushing medium into a third conduit in fluid communication with a third adsorbent bed chamber to flush residue of the first flushing medium from the third conduit into the adsorbent bed of the third adsorbent bed chamber, wherein the third adsorbent bed chamber is located upstream from the second adsorbent bed chamber, based on the direction of the flow of the circulating bulk fluid;
  wherein the second flushing medium comprises less than 1 volume percent of ethylbenzene, less than 2 volume percent of orthoxylene, and less than 2 volume percent of metaxylene; and
  (d) withdrawing an extract stream comprising paraxylene from a fourth adsorbent bed in a fourth adsorbent bed chamber through a fourth conduit in fluid communication with the fourth adsorbent bed chamber wherein the fourth adsorbent bed chamber is located upstream from the third adsorbent bed chamber, based on the direction of the flow of the circuiting bulk fluid.

19. The process of claim 18, wherein the at least one refinery or petrochemical process for producing the at least 50 volume percent of the C8 aromatic mixture in the multicomponent feed of step (a), which mixture comprises from 15 to 30 volume percent of paraxylene, comprises at least one process selected from the group consisting of a reforming process, an isomerization process and a transalkylation process, and wherein the at least one refinery or petrochemical process for producing the 10 to 95 volume percent of the C8 aromatic mixture in the first flushing medium of step (a), which mixture comprises from 75 to 98 volume percent of paraxylene, comprises a selective toluene disproportionation process.

20. A process for making paraxylene, said process comprising the steps of:
  (i) forming a first mixture of C8 aromatics by at least one process for producing equilibrium xylenes, selected from the group consisting of a reforming process, a transalkation process and an isomerization process, wherein the first mixture of C8 aromatics comprises from 15 to 30 volume percent of paraxylene;
  (ii) forming a second mixture of C8 aromatics by at least one process for producing enhanced paraxylene, selected from the group consisting of a toluene disproportion process and a toluene alkylation process, wherein the second mixture of C8 aromatics comprises from 75 to 98 volume percent of paraxylene;
  (iii) passing at least a portion of the first mixture of C8 aromatics from step (i) through a rotary valve and then through a first conduit and then into a first bed of a simulated countercurrent adsorptive separation unit, wherein the simulated countercurrent adsorptive separation unit comprises a series of beds of adsorbent, wherein the beds are stacked one on top of another, wherein liquid flows continuously in a downward manner from the top of one bed, through the bed, and then to the top of the next bed immediately below, and wherein the affinity of the adsorbent in the beds to adsorb paraxylene is greater the affinity of the adsorbent to adsorb any of metaxylene, orthoxylene, and ethylbenzene;
  (iv) passing at least a portion of the second mixture of C8 aromatics from step (ii) through a rotary valve and then through a second conduit in fluid communication with the rotary valve and a second bed of the simulated countercurrent adsorptive separation unit, wherein the first bed of step (iii) is different than the second bed of step (iv), wherein the first bed of step (iii) is located downstream, based on the direction of the flow of continuously flowing liquid, from the second bed of step (iv), and wherein the volume of the second mixture of C8 aromatics from step (ii) introduced into the second conduit is less than the total volume of the second conduit;
  (v) passing a liquid through a rotary valve and then through a third conduit in fluid communication with the rotary valve and a third bed of the simulated countercurrent adsorptive separation unit, wherein the first bed of step (iii) and the second bed of step (iv) are both different than the third bed of step (v), wherein the second bed of step (iv) is located downstream, based on the direction of the flow of continuously flowing liquid, from the third bed of step (v), and wherein the liquid passed into the third conduit of step (v) comprises less than 1 volume percent of ethylbenzene, less than 2 volume percent of orthoxylene, and less than 2 volume percent of metaxylene;

(vi) withdrawing an extract stream comprising a desorbent and paraxylene from a fourth bed of the simulated countercurrent adsorptive separation unit, through a fourth conduit and then through a rotary valve, wherein the first bed of step (iii), the second bed of step (iv) and the third bed of step (v) are all different than the fourth bed of step (vi), wherein the third bed of step (v) is located downstream, based on the direction of the flow of continuously flowing liquid, from the fourth bed of step (vi); and (vi) passing desorbent through a rotary valve and then through a fifth conduit and then into a fifth bed of the simulated countercurrent adsorptive separation unit, wherein the first bed of step (iii), the second bed of step (iv), the third bed of step (v) and the fourth bed of step (vi) are all different than the fifth bed of step (vii), wherein the fourth bed of step (vi) is located downstream, based on the direction of the flow of continuously flowing liquid, from the fifth bed of step (vii).

21. The process of claim 20, wherein said reforming process comprises passing naphtha into a reforming unit, converting at least a portion of the naphtha in the reforming unit into aromatic compounds comprising benzene, toluene, xylenes, and ethylbenzene, and separating xylenes and ethylbenzene from other aromatics by a distillation process.

22. The process of claim 20, wherein said transalkylation process comprises passing a mixture of toluene and trimethylbenzene into a transalkylation unit, converting at least a portion of the toluene and trimethylbenzene in the transalkylation unit into aromatic compounds comprising xylenes and ethylbenzene.

23. The process of claim 20, further comprising the step of:

(vii) withdrawing a raffinate steam comprising a desorbent, metaxylene, orthoxylene, and ethylbenzene from a sixth bed of the simulated countercurrent adsorptive separation unit, through a sixth conduit and then through a rotary valve, wherein the first bed of step (iii), the second bed of step (iv), the third bed of step (v), the fourth bed of step (vi) and the fifth bed of step (vii) are all different than the sixth bed of step (vii), wherein the sixth bed of step (vii) is downstream, based on the direction of the flow of continuously flowing liquid, from the first bed of step (iii), and wherein the raffinate stream comprises desorbent, metaxylene, orthoxylene, and ethylbenzene;

(ix) distilling the raffinate stream from step (viii) to obtain a steam enriched in desorbent and a steam enriched in C8 aromatics comprising metaxylene, orthoxylene, and ethylbenzene;

(x) passing the stream enriched in C8 aromatics from step (ix) to an isomerization unit to obtain an isomerized product steam comprising from 15 to 30 volume percent of paraxylene; and (xi) passing at least a portion of isomerized product steam from step (x) to the adsorbent bed of step (iii).

24. The process of claim 20, wherein, over time, the flow of liquids, other than circulating bulk fluid, into and out of the beds of the steps of claim 23 is discontinued and the flow of liquids into and out of the beds is resumed in the next beds in the series downstream, in terms of the flow of circulating fluid, of the steps of claim 23.

* * * * *